(12) United States Patent
Taskén et al.

(10) Patent No.: US 7,790,738 B2
(45) Date of Patent: Sep. 7, 2010

(54) METHODS OF TREATING AND PREVENTING AIDS USING OF COX-2 INHIBITORS

(75) Inventors: Kjetil Taskén, Rykkinn (NO); Michel Moutschen, Neupré (BE); Souad Rahmouni-Piette, Seraing (BE); Einar Martin Aandahl, Lillehammer (NO); Pål Aukrust, Ridabu (NO); Stig S. Frøland, Oslo (NO); Christian C. Johansson, Oslo (NO); Vidar Hansson, Sandvika (NO); Jo Klaveness, Oslo (NO)

(73) Assignee: Lauras AS, Oslo (NO)

( * ) Notice: Subject to any disclaimer, the term of this patent is extended or adjusted under 35 U.S.C. 154(b) by 39 days.

(21) Appl. No.: 10/333,657

(22) PCT Filed: Jul. 20, 2001

(86) PCT No.: PCT/GB01/03284

§ 371 (c)(1),
(2), (4) Date: Jun. 6, 2003

(87) PCT Pub. No.: WO02/07721

PCT Pub. Date: Jan. 31, 2002

(65) Prior Publication Data

US 2004/0082640 A1    Apr. 29, 2004

(30) Foreign Application Priority Data

Jul. 20, 2000  (GB) .................................. 0017908.5
Apr. 19, 2001  (GB) .................................. 0109648.6

(51) Int. Cl.
*A01N 43/40* (2006.01)
*A01N 43/82* (2006.01)
*A01N 43/78* (2006.01)
*A01N 43/56* (2006.01)
*A01N 43/36* (2006.01)
*A01N 43/02* (2006.01)
*A61K 31/435* (2006.01)
*A61K 31/41* (2006.01)
*A61K 31/425* (2006.01)
*A61K 31/40* (2006.01)
*A61K 31/38* (2006.01)
*A61K 31/335* (2006.01)

(52) U.S. Cl. ........................ 514/277; 514/360; 514/364; 514/365; 514/403; 514/427; 514/430; 514/449

(58) Field of Classification Search ............... 424/188.1; 514/468, 277, 360, 364, 365, 403, 427, 430, 514/449
See application file for complete search history.

(56) References Cited

U.S. PATENT DOCUMENTS

| | | | |
|---|---|---|---|
| 5,344,991 A | 9/1994 | Reitz et al. | |
| 5,380,738 A | 1/1995 | Norman et al. | |
| 5,393,790 A | 2/1995 | Reitz et al. | |
| 5,434,178 A | 7/1995 | Talley et al. | |
| 5,474,995 A | 12/1995 | Ducharme et al. | |
| 5,475,018 A | 12/1995 | Lee et al. | |
| 5,510,368 A | 4/1996 | Lau et al. | |
| 5,527,713 A * | 6/1996 | Bolton et al. | ............... 436/529 |
| 5,643,960 A | 7/1997 | Breitner et al. | |
| 5,716,955 A | 2/1998 | Adams et al. | |
| 5,776,940 A | 7/1998 | Daluge et al. | |
| 5,811,549 A | 9/1998 | Adams et al. | |
| 6,025,353 A | 2/2000 | Masferrer et al. | |
| 6,306,842 B1 * | 10/2001 | Lai et al. | ..................... 514/159 |
| 6,420,403 B1 * | 7/2002 | Iwanowicz et al. | .......... 514/374 |
| 2003/0138399 A1 * | 7/2003 | Anton et al. | ............... 424/85.1 |

FOREIGN PATENT DOCUMENTS

| | | |
|---|---|---|
| EP | 0 595 546 | 5/1994 |
| EP | 0 673 366 | 9/1995 |
| EP | 1288206 | 3/2003 |
| JP | 10175861 | 6/1998 |
| WO | WO 92/10190 | 6/1992 |
| WO | WO 94/03448 | 2/1994 |
| WO | WO 94/13635 | 6/1994 |
| WO | WO 94/15932 | 7/1994 |
| WO | WO 94/20480 | 9/1994 |
| WO | WO 94/26781 | 11/1994 |
| WO | WO 94/27980 | 12/1994 |
| WO | WO 95/00501 | 1/1995 |
| WO | WO 95/15316 | 6/1995 |
| WO | WO 95/21817 | 8/1995 |
| WO | WO 95/23139 | 8/1995 |

(Continued)

OTHER PUBLICATIONS

Crofford; COX-1 and COX-2 tissue expression: implications and predictions, *J Rheumatol*, 24 Suppl 49: 15-9 (1997).

(Continued)

*Primary Examiner*—Yong S Chong
(74) *Attorney, Agent, or Firm*—Kenyon & Kenyon LLP

(57) ABSTRACT

The present invention provides a method of treating or preventing a disorder typified by an immunodificiency (e.g. HIV), wherein the patient is administered a COX-2 inhibitor or derivative or pharmaceutically acceptable salt thereof, preferably diisopropylfluorophasphate. L-745337, rofecoxib, NS 398, SC 58125, etodolac, meloxicam, celecoxib or nimesulide, and compositions and products containing the same or use of the same in preparing medicaments and for treatment.

23 Claims, 13 Drawing Sheets

FOREIGN PATENT DOCUMENTS

Figure 1:
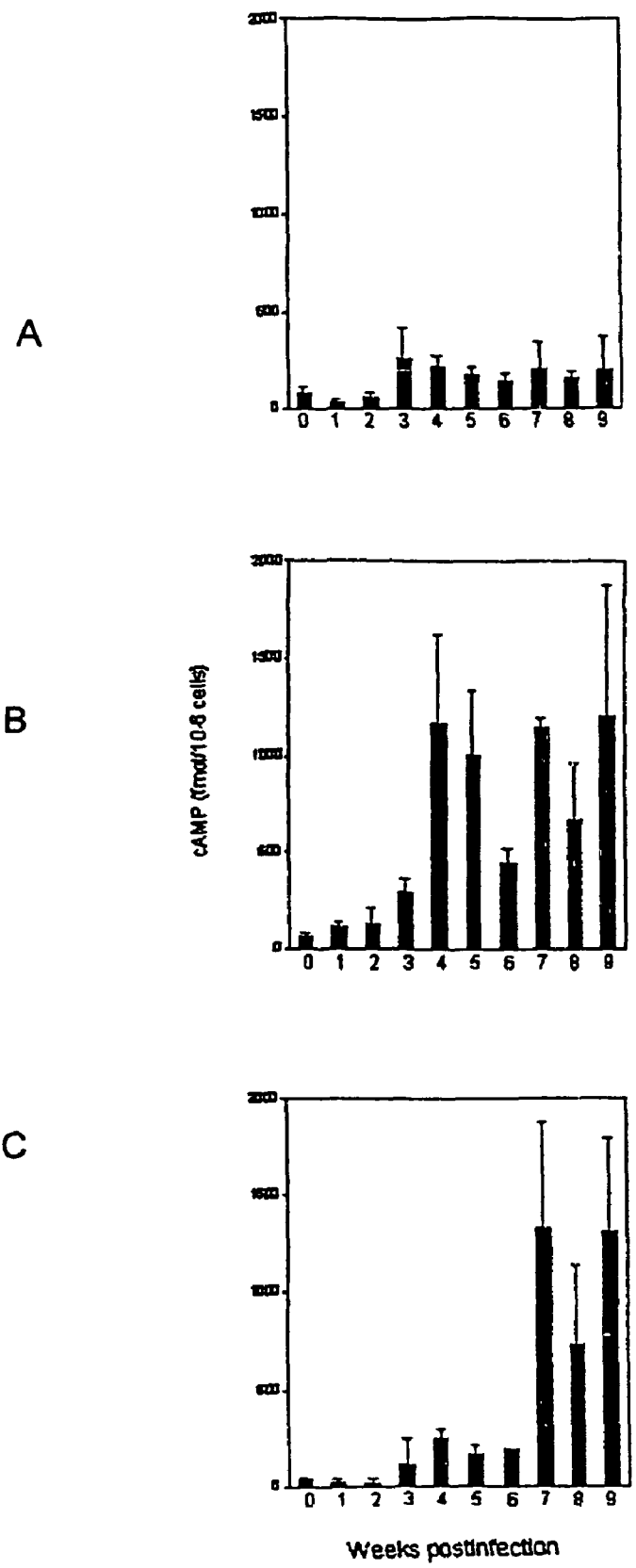

| WO | WO 96/03385 | 2/1996 |
|---|---|---|
| WO | WO 96/03387 | 2/1996 |
| WO | WO 96/03388 | 2/1996 |
| WO | WO 96/03392 | 2/1996 |
| WO | WO 96/04280 | 2/1996 |
| WO | WO 96/06840 | 3/1996 |
| WO | WO 96/16934 | 6/1996 |
| WO | WO 96/16943 | 6/1996 |
| WO | WO 96/21452 | 7/1996 |
| WO | WO 96/25105 | 8/1996 |
| WO | WO 96/25405 | 8/1996 |
| WO | WO 96/31509 | 10/1996 |
| WO | WO 97/03678 | 2/1997 |
| WO | WO 97/25046 | 7/1997 |
| WO | WO 97/29774 | 8/1997 |
| WO | WO 98/01443 | 1/1998 |
| WO | WO 98/06715 | 2/1998 |
| WO | WO 98/07714 | 2/1998 |
| WO | WO 98/20864 | 5/1998 |
| WO | WO 98/28292 | 7/1998 |
| WO | WO 98/41511 | 9/1998 |
| WO | WO 98/41516 | 9/1998 |
| WO | WO 98/43966 | 10/1998 |
| WO | WO 98/45294 | 10/1998 |
| WO | WO 98/47871 | 10/1998 |
| WO | WO 99/12930 | 3/1999 |
| WO | WO 99/14194 | 3/1999 |
| WO | WO 99/14195 | 3/1999 |
| WO | WO 99/15503 | 4/1999 |
| WO | WO 99/15513 | 4/1999 |
| WO | WO 99/20110 | 4/1999 |
| WO | WO 99/23087 | 5/1999 |
| WO | WO 00/40243 | 7/2000 |
| WO | WO 00/69255 | 11/2000 |
| WO | WO 01/41536 | 6/2001 |
| WO | WO 02/07721 A2 | 1/2002 |
| WO | WO 02/07721 A3 | 1/2002 |

OTHER PUBLICATIONS

Crofford; Specific cyclooxygenase-2 inhibitors: what have we learned since they came into widespread clinical use?, *Curr. Opin Rheumatol*, 14(3): 225-30, (2002).

De Gregorio et al.; Cot Kinase Induces Cyclooxygenase-2 Expression in T Cells through Activation of the Nuclear Factor of Activated T Cells, *J. of Biological Chemistry*, 276(29): 27003-27009, (2001).

Delemarre et al.; Reduced toxoplasmastatic activity of monocytes and monocyte-derived macrophages from AIDS patients is mediated via prostaglandin E2, *AIDS*, 9(5): 441-5, (1995).

DuBois et al.; Cyclooxygenase in biology and disease, *J. FASEB*, 12, 1063-1073, (1998).

Iniguez et al.; An Essential Role of the Nuclear Factor of Activated T Cells in the Regulation of the Expression of the Cyclooxygenase-2 Gene in Human T Lymphocytes, *J. of Biological Chemistry*, 275(31): 23672-23635, (2000).

Nataraj et al.; Receptors for prostaglandin $E_2$ that regulate cellular immune responses in the mouse, *J. of Clinical Investigation*, 108: 1229-1235, (2001).

Pablos et al., Cyclooxygenase-1 and -2 are expressed by human T cells, *J. Clin. Exp. Immunol.*, 115(1): 86-90 (1999).

Rahmouni et al.; Increased cAMP levels and protein kinase (PKA) type I activation in $CD4^+$ T cells and B cells contribute to the retrovirus-induced immunodeficiency of mice (MAIDS). A useful in vivo model for drug testing in PKA type I-induced immunodeficiency, *FASEB J.* (published online Apr. 27, 2001).

Stadler et al., Pentoxifylline and Meclofenamic Acid Treatment Reduces Clinical Manifestations in a Murine Model of AIDS, *J Pharmacol Exp Ther*, 268(1): 10-13 (1994).

Valone et al., Indomethacin Enhances the Proliferation of Mitogen-Stimulated T Lymphocytes of Homosexual Males with Persistent Generalized Lymphadenopathy, *J Clin Immunol* 4(5): 383-387 (1984).

Vane and Botting; Mechanism of Action of Anti-Inflammatory Drugs, *Scand J Rheumatol* 25(Suppl 102): 9-21 (1996).

Warner et al.; Nonsteroid drug selectivities for cyclo-oxygenase-1 rather than cyclo-oxygenase-2 are associated with human gastrointestinal toxicity: A full in vitro analysis, *Proc. Natl. Acad. Sci USA*, 96, 7563-7568, (1999).

Bagetta, G. et al, HIV-1 gp120-Induced Apoptosis in the Rat Neocortex Involves Enhanced Expression of Cyclo-oxygenase Type 2 (COX-2), Biochem. and Biophys. Res. Comm. (1998) vol. 244:3 pp. 819-824 (Database Biosis 'Online!, Bioscience Information Service).

Schroder, Heinz C. et al, "Avarol restores the altered prostaglandin and leukotriene metabolism in monocytes infected with human immunodeficiency virus type 1", Virus Research, vol. 21:3 (Nov. 1991), pp. 213-224. (Database Biosis 'Online!, Bioscience Information Service).

Ambrus Jr., Julian L. et al, Improved in vitro antigen-specific antibody synthesis in two patients with common variable immunodeficiency taking an oral cyclooxygenase and lipoxygenase inhibitor (ketoprofen), J. of Allergey and Clinical Immunology, (Nov. 1991) vol. 88:5 pp. 775-783. (Database Biosis 'Online!, Bioscience Information Service).

Foster, Steven H. et al, "Cyclooxygenase inhibition and improved oxygenation in patients with pulmonary complications of AIDS" NYS J. of Medicine, (May 1987) vol. 87:5 pp. 280-282. (Database Biosis 'Online!, Bioscience Information Service).

Woloschak, Gayle E. et al., "Salicylic Acid Inhibits Ultraviolet- and cis-Platinum-induced Human Immunodeficiency Virus Expression", Cancer Research (Apr. 15, 1995) vol. 55:8 pp. 1696-1700. (Database Biosis 'Online!, Bioscience Information Service).

Corasaniti, M. T. et al "Neurobiological mediators of gp120-induced apoptosis in the brain cortex of rat", J. of Neurovirology, (Jun. 2000) vol. 6:3 pp. 258. (Print Meeting Info.: Neuroscience of HIV Infection 2000).

Iniguez, M. A. et al. "Induction of Cyclooxygenasae-2 on Activated T Lymphocytes: Regulation of T Cell Activation by Cyclooxygenase-2 Inhibitors", J. of Immunology, (1999) vol. 163:1, pp. 111-119.

Rioux, Nathalie et al. "Recovery from 4-(methylnitrosamino)-1-(3-pyridyl)-1-buta none-induced immunosuppression in A/J mice by treatment with nonsteroidal anti-inflammatory drugs", J. Natl. Cancer Inst. (1997) vol. 89:12, pp. 874-880.

Lis, T. et al, "Inhibition of immune response by diisopropyl phosphorofluoridate" , Arch. Toxicol., Suppl. (1980), vol. 4, pp. 151-155.

Kamoshita, K. et al, "Calicium requirement and inhibitor spectrum for intracellular HIV type 1 gp160 processing in cultured HeLa cells and CD4+ lymphocytes: Similarity to those of viral envelope glycoprotein maturase" J. of Biochemistry, (1995) vol. 117:6, pp. 1244-1253.

Speir, Edith, et al "Aspirin attenuates cytomegalovirus infectivity and gene expression mediated by cyclooxygenase-2 in coronary artery smooth muscle cells" Circ. Res. (1998) vol. 83:2 pp. 210-216.

Aziz et al., *Severe Immunodeficiency Disease Induced by a Defective Murine Leukaemia Virus*, Nature,vol. 338, Apr. 1989, pp. 505-508.

Battistini et al., *COX-1 and COX-2: Toward the Development of More Selective NSAIDs*, Prous Science Drug News and Perspectives, 7(8), Oct. 1994, pp. 501-512.

Betz et al., *Prostaglandin E2 Inhibits Production of Th1 Lymphokines But Not of Th2 Lymphokines*, Journal of Immunology, vol. 146, No. 1, Jan. 1991, pp. 108-113.

Bjarnason et al., *A Randomized, Double-Blind, Crossover Comparative Endoscopy Study on the Gastroduodenal Tolerability of a Highly Specific Cyclooxygenase-2 Inhibitor, Flosulide, and Naproxen*, Scand. J. of Gastroenterology, vol. 32, 1997, pp. 126-130.

Black et al., *2,3-Diarylcyclopentenones as Orally Active, Highly Selective Cyclooxygenase-2 Inhibitors*, J. Med. Chem., vol. 42, Mar. 1999, pp. 1274-1281.

Brettle et al., *Combination Therapy for HIV: the Effect on Inpatient Activity, Morbidity and Mortality of a Cohort of Patients*, Int. J. STD AIDS, vol. 9, Feb. 1998, pp. 80-87.

Chan et al., *Pharmacology of a Selective Cyclooxygenase-2 Inhibitor, L-745, 337: A Novel Nonsteroidal Anti-inflammatory Agent with an Ulcerogenic Sparing Effect in Rat and Nonhuman Primate Stomach*, J. Pharmacol. Exp. Ther., vol. 274, No. 3, May 1995, pp. 1531-1537.

Chattopadhyay et al., *Characteristics and Contributions of Defective, Ecotropic, and Mink Cell Focus-Inducing Viruses Involved in a Retrovirus-Induced Immunodeficiency Syndrom of Mice*, J. Virol., vol. 65, No. 8., Aug. 1991, pp. 4232-4241.

Dallob et al., *Ex Vivo Assays Demonstrate Potency and Selectivity of the COX-2 Inhibitor DFP After Single Dose Administration*, 9$^{th}$ Intern. Conference Inflamm. Res. Assoc., Nov. 1-5, 1998.

Dannenberg et al., *Chemoprevention of Colorectal Cancer Through Inhibition of Cyclooxygenase-2*, Semin. Oncol., vol. 26, Oct. 1999, pp. 499-504.

De Clercq, *The Role of Non-Nucleoside Reverse Transcriptase Inhibitors (NNRTIs) in the Therapy of HIV-1 Infection*, Antiviral Res., vol. 38, 1998, pp. 153-179.

De Leval et al., *CD28-B7 Costimulatory Blockade by CTLA4Ig Delays the Development of Retrovirus-Induced Murine AIDS*, J. Virol., vol. 72, No. 6, Jun. 1998, pp. 5285-5290.

Ehrich et al., *MK-966, A Highly Selective COX-2 Inhibitor, Was Effective in the Treatment of Osteoarthritis (OA) of the Knee and Hip in a 6-Week Placebo Controlled Study*, Arthritis Rheum., vol. 40, 1997, S93.

Engelhardt et al., *Anti-Inflammatory, Analgesic, Antipyretic and Related Properties of Meloxicam, a New Non-Steroidal Anti-Inflammatory Agent with Favourable Gastrointestinal Tolerance*, Inflamm. Res., vol. 44, 1995, pp. 423-433.

Fedyk et al., *Prostoglandin E2 Receptors of the EP2 and EP4 Subtypes Regulate Activation and Differentiation of Mouse B Lymphocytes to IgE-Secreting Cells*, Proc. Natl. Acad. Sci. USA, vol. 93, Oct. 1996, pp. 10978-10983.

Futaki et al., *NS-398, A New Anti-Inflammatory Agent, Selectively Inhibits Prostaglandin G/H Synthase/Cyclooxygenase (COX-2) Activity in Vitro*, Prostaglandins, vol. 47, Jan. 1994, pp. 55-59.

Futaki et al., *Selective Inhibition of NS-398 on Prostanoid Production in Inflamed Tissue in Rat Carrageenan-Air-Pouch Inflammation*, J. Pharm. Pharmacol., vol. 45, 1993, pp. 753-755.

Gait et al., *Progress in Anti-HIV Structure-Based Drug Design*, Tibtech, vol. 13, Oct. 1995, pp. 430-438.

Geis, *Update on Clinical Developments With Celecoxib, A New Specific COX-2 Inhibitor: What Can We Expect?*, Scand. J. Rheumatol., vol. 109 (Suppl.), 1999, pp. 31-37.

Golden et al., *Selective Cyclooxygenase-2 Inhibitors*, Rheumatic Disease Clinics of North America, vol. 25, No. 2, May 1999, pp. 359-379.

Green et al., *Antibody to the Ligand for CD40 (gp39) Inhibits Murine AIDS-Associated Splenomegaly, Hypergammaglobulinemia, and Immunodeficiency in Disease-Susceptible C57BL/6 Mice*, J. Virol., vol. 70, No. 4, Apr. 1996, pp. 2569-2575.

Griswold et al., *Constitutive Cyclooxygenase (COX-1) and Inducible Cyclooxygenase (COX-2): Rationale for Selective Inhibition and Progress to Date*, Med. Res. Rev., vol. 16, No. 2, 1996, pp. 181-206.

Guo et al., *Role of Val509 in Time-Dependent Inhibition of Human Prostaglandin H Synthase-2 Cyclooxygenase Activity by Isoform-selective Agents*, J. Biol. Chem., vol. 271, No. 32, Aug. 1996.

Holmes, et al., *A Unique Subset of Normal Murine CD4+ T Cells Lacking Thy-1 is Expanded in a Murine Retrovirus-Induced Immunodeficiency Syndrome, MAIDS*, Eur. J. Immunol., vol. 20, 1990, pp. 2783-2787.

Jolicoeur, *Murine Acquired Immunodeficiency Syndrome (MAIDS): An Animal Model to Study the AIDS Pathogenesis*, The FASEB Journal, vol. 5, Jul. 1991, pp. 2398-2405.

Kammer, *The Adenylate Cyclase—cAMP—Protein Kinase A Pathway and Regulation of the Immune Response*, Immunol. Today, vol. 9, Nos. 7 and 8, 1988, pp. 222-229.

Klein et al., *Selective Inhibition of Cyclooxygenase 2*, Biochem. Pharmacol., vol. 48, No. 8, 1994, pp. 1605-1610.

Klein et al., *Mechanistic Studies on the Selective Inhibition of Cylcooxygenase-2 by Indanone Derivatives*, Biochem. Pharmacol., vol. 51, 1996, pp. 285-290.

Kolenko et al., *Downregulation of JAK3 Protein Levels in T Lymphocytes by Prostaglandin E2 and Other Cyclic Adenosine Monophosphate-Elevating Agents: Impact on Interleukin-2 Receptor Signaling Pathway*, Blood, vol. 93, No. 7, Apr. 1999, pp. 2308-2318.

Lane, *Pain Management in Osteoarthritis: The Role of COX-2 Inhibitors*, J. Rhemmatol., vol. 24, 1997, pp. 20-24.

Laneuvill et al., *Differential Inhibition of Human Prostaglandin Endoperoxide H Synthases-1 and -2 by Nonsteroidal Anti-Inflammatory Drugs*, J. Pharm. Exp. Ther., vol. 271, No. 2, 1994, pp. 927-934.

Levi et al., *Regulation of Prostanoid Synthesis in Microglial Cells and Effects of Prostaglandin E2 on Microglial Functions*, Biochimic, vol. 80, 1998, pp. 899-904.

Masferrer et al., *Selective Inhibition of Inducible Cyclooxygenase 2 in vivo is Antiinflammatory and Nonulcerogenic*, Proc. Natl. Acad. Sci., vol. 91, Apr. 1994, pp. 3228-3232.

Maziasz et al., *Preclinical Pharmacology of Celecoxib and Demonstration of Superior GI Safety Compared with NSAIDs in Dogs*, Arthritis Rheum., vol. 40, 1997, p. S195.

Mehlish et al., *Ex Vivo Assay of COX-2 Inhibition Predicts Analgesic Efficacy in Post-Surgical Dental Pain with MK-966*, Clin. Pharmacol. Ther., vol. 63, No. 2, 1998, pp. 139, PI-8.

Mengle-Gaw et al., *A Study of the Platelet Effects of SC-58635, A Novel COX-2-Selective Inhibitor*, Arthritis Rheum., vol. 40, 1997, p. S93.

Meyaard et al., *Interleukin-12 (IL-12) Production in Whole Blood Cultures From Human Immunodeficiency Virus-Infected Individuals Studied in Relation to IL-10 and Prostaglandin E2 Production*, Blood, vol. 89, No. 2, Jan. 1997, pp. 570-576.

Mitchell et al., *Cyclo-oxygenase-2: Pharmacology, Physiology, Biochemistry and Relevance to NSAID Therapy*, Brit. J. Pharmacol., vol. 128, 1999, pp. 1121-1132.

Mitchel et al., *Selectivity of Nonsteroidal Antiinflammatory Drugs as Inhibitors of Constitutive and Inducible Cyclooxygenase*, Proc. Natl. Acad. Sci., vol. 90, Dec. 1994, pp. 11693-11697.

Morrison et al., *Analgesic Efficacy of the Cyclooxygenase-2-Specific Inhibitor Rofecoxib in Post-Dental Surgery Pain: A Randomized, Controlled Trial*, Clin. Ther., vol. 21, No. 6, 1999, pp. 943-953.

Moutschen et al., *Population Dynamics of CD4+ T Cells Lacking Thy-1 in Murine Retrovirus-Induced Immunodeficiency Syndrome (MAIDS)*, Scand. J. Immunol., vol. 39, 1994, pp. 216-224.

Penning et al., *Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib)*, J. Med. Chem., 1997, pp. 1347-1365.

Puig et al., *Synthesis and Biological Evaluation of 3,4-Diaryloxazolones: A New Class of Orally Active Cyclooxygenase-2 Inhibitors*, J. Med. Chem., vol. 43, 2000, pp. 214-223.

Redshaw et al., *Human Immunodeficiency Virus Protease Inhibitors, Emerging Drugs: The Prospect for Improved Medicines*, Chapter 6, 1997, pp. 127-154.

Reitz et al., *Selective Cyclooxygenase Inhibitors: Novel 1,2-Diarylcyclopentenes are Potent and Orally Active COX-2 Inhibitors*, J. Med. Chem., vol. 37, 1994, pp. 3878-3881.

Reitz et al., *Selective Cyclooxygenase Inhibitors*, Ann. Rep. Med. Chem., vol. 30, 1995, pp. 179-188.

Riendeau et al., *Biochemical and Pharmacological Profile of a Tetrasubstituted Furanone as a Highly Selective COX-2 Inhibitor*, British J. Pharmacol., vol. 121, 1997, pp. 105-117.

Seibert et al., *Pharmacological and Biochemical Demonstration of the Role of Cyclooxygenase 2 in Inflammation and Pain*, Proc. Natl. Acad. Sci. USA, vol. 91, Dec. 1994, pp. 12013-12017.

Simard et al., *Murine AIDS is Initiated in the Lymph Nodes Draining the Site of Inoculation, and the Infected B Cells Influence T Cells Located at Distance, in Noninfected Organs*, J. Virol., vol. 68, No. 3, Mar. 1994, pp. 1903-1912.

Smith et al., *Prostaglandin Endoperoxide H Synthases-1 and -2*, Adv. Immunol., vol. 62, 1996, pp. 167-215.

Taketo, *Cyclooxygenase-2 Inhibitors in Tumorigenesis (Part I)*, J. National Cancer Inst., vol. 90, No. 20, Oct. 1998, pp. 1529-1536.

Taskén et al., *Novel Isozymes of cAMP-dependent Protein Kinase Exist in Human Cells Due to Formulation of RIα-RIβ Heterodimeric Complexes*, J. Biol. Chem., vol. 268, No. 28, Oct. 1995, pp. 21276-21283.

Vane et al., *Cyclooxygenases 1 and 2*, Annu. Rev. Pharmacol. Toxicol., vol. 38, 1998, pp. 97-120.

Vane, *Towards a Better Aspirin*, Nature, vol. 367, Jan. 1994, pp. 215-216.

Warner et al., *Nonsteroid Drug Selectivities for Cyclo-oxygenase-1 Rather Than Cyclo-Oxygenase-2 are Associated with Human Gastrointestinal Toxicity: A Full in vitro Analysis*, Proc. Natl. Acad. Sci. USA, vol. 96, Jun. 1999, pp. 7563-7568.

Williams et al., *The Role of Cyclooxygenases in Inflammation, Cancer, and Development*, Oncogene, vol. 18, 1999, pp. 7908-7916.

Zhao et al., *Effect of Celecoxib, A Novel COX-2 Inhibitor, On Health-Related Quality of Life of Patients with Osteoarthritis of the Knee*, Arthritis Rheum., vol. 40, 1997, p. S88.

Hilger, New Nucleoside Analogs for Treatment of Viral Diseases in Review, Pharmazie Unserer Zeit, May 1998; 27 (3): 111-116.

Hilger, HIV-1 Protease Inhibitors in Review, Pharmazie Unserer Zeit, Jan. 1998; 27(1): 22-25.

Stellbrink, Chemotherapy for HIV-1 Infection, Deutsches Arzteblatt, 94, vol. 39 (53), Sep. 26, 1997; 2497-2503.

Wajeman-Chao, S. A. et al., "Mechanism of catecholamine-mediated destabilization of messenger RNA encoding Thy-1 protein in T-lineage cells", J. Immunol. (1998), vol. 161:9, pp. 4825-4833.

Lipsky, P. E., "The clinical potential of cyclooxygenase-2-specific inhibitors", (1999), Am. J. Med., vol. 106:5B, pp. 51S-57S.

* cited by examiner

METHODS OF TREATING AND PREVENTING AIDS USING OF COX-2 INHIBITORS

The invention is in the field of treatment of immunodeficiencies and viral infections. More specifically, the invention relates to the use of cyclooxygenase-2 (COX-2) inhibitors or derivatives thereof in immunomodulation for treatment of immunodeficiency and viral diseases; especially HIV infection and AIDS and related conditions.

Prostaglandins play an important role in the inflammation process and inhibition of formation of prostaglandins has been a popular target for development of anti-inflammatory drugs. Non-steroid anti-inflammatory drugs (NSAID's) inhibit cyclooxygenase (COX) which is an enzyme involved in the biosynthesis of prostaglandin intermediates from arachidonic acid. There are several NSAID's in clinical use including drugs like indomethacin, piroxicam, tenoxicam, diclofenac, meloxicam, tenidap, isoxicam, acetylsalicylic acid, diflunisal, sulindac, ibuprofen, naproxen and ketoprofen.

NSAID's are today among the most widely prescribed drugs worldwide.

These NSAID's are clinically efficient drugs and they possess antipyretic, anti-inflammatory and antithrombotic effects. The main indications for this class of drugs are arthritis including osteoarthritis and rheumatoid arthritis, painful musculoskeletal conditions and general pain conditions. However, there are severe side-effects with these drugs. The most frequent side effects are gastrointestinal ulceration and bleeding, inhibition of platelet aggregation and interaction with other drugs.

In the early 1990's a second COX isoform of the enzyme was cloned. This new COX isoform is now known as COX-2 (Vane et al, 1998, Ann. Rev. Pharmacol. Toxicol., 38, p97-120).

There are now two well known isoforms of COX, COX-1 and COX-2 (recently the existence of COX-3 has also been postulated). COX-1 is present in most tissues and can be regarded as the housekeeper enzyme. The activity of the COX-1 enzyme protects, for example, the lining in the gastrointestinal tract. COX-2, however, is not present normally but increases during inflammation. Several of the side effects of NSAID's are related to inhibition of COX-1 enzyme. NSAID's inhibit both COX-1 and COX-2 (see Tables 1-3):

TABLE 1

$IC_{50}$ values and COX-2/COX-1 ratios of different NSAID's in guinea pig macrophage model ($IC_{50}$ values from Engelhart et al. in J. Inflammatory Res., 44, p 422-43, 1995)

| NSAID'S | COX-2 $IC_{50}$ (µmol/litre) | COX-1 $IC_{50}$ (µmol/litre) | COX-2 selectivity COX-1/COX-2 |
|---|---|---|---|
| Meloxicam | 0.0019 | 0.00577 | 3 |
| Diclofenac | 0.0019 | 0.000855 | 0.45 |
| Piroxicam | 0.175 | 0.00527 | 0.030 |
| Tenoxicam | 0.322 | 0.201 | 0.6 |
| Indomethacin | 0.00636 | 0.00021 | 0.03 |
| Teridep | 47.8 | 0.393 | 0.008 |

TABLE 2

$IC_{50}$ values for NSAID's in intact cell on COX-1 (bovine endothelial cells) and COX-2 (stimulated macrophages) ($IC_{50}$ values from Taketo in J. National Cancer Institute, 90, p 1529-1536, 1998)

| NSAID'S | COX-2 $IC_{50}$ (µmol/litre) | COX-1 $IC_{50}$ (µmol/litre) | COX-2 selectivity COX-1/COX-2 |
|---|---|---|---|
| Asprin | 50 | 0.3 | 0.006 |
| Indomethacin | 0.6 | 0.01 | 0.02 |
| Tolfenamic acid | 0.005 | 0.0003 | 0.06 |
| Ibuprofen | 15 | 1 | 0.07 |
| Acetaminophen | 20 | 2.7 | 0.1 |
| Sodium salicylate | 100 | 35 | 0.35 |
| BW 755C | 1.2 | 0.65 | 0.5 |
| Flubiprofen | 0.025 | 0.02 | 0.8 |
| Carprofen | 3 | 3 | 1 |
| Diclofenac | 0.35 | 0.5 | 1.4 |
| Naproxen | 1.3 | 2.2 | 1.7 |
| BF 389 | 0.03 | 0.15 | 5 |

TABLE 3

Inhibition of recombinant human PGH synthesis (COX-1 and COX-2) ($IC_{50}$ values from Laneuvill et al. in J. Pharm. Exp. Ther., 271, p 927-34, 1994)

| NSAID'S | COX-2 $IC_{50}$ (µmol/litre) | COX-1 $IC_{50}$ (µmol/litre) | COX-2 selectivity COX-1/COX-2 |
|---|---|---|---|
| Indomethacin | >1000 | 13.5 | <0.01 |
| Sulindac sulphide | 50.7 | 1.3 | 0.03 |
| Piroxicam | >500 | 17.7 | 0.04 |
| Diclofenac | 20.5 | 2.7 | 0.13 |
| Flubiprofen | 3.2 | 0.5 | 0.16 |
| Meclofenemate | 9.7 | 1.5 | 0.15 |
| Phenylbutazone | >100 | 16.0 | <0.16 |
| Naproxen | 28.4 | 4.8 | 0.17 |
| Ibuprofen | 12.5 | 4.0 | 0.3 |
| Ketorolac tromethamine | 60.5 | 31.5 | 0.5 |
| DHA (22:6) | 41 | 25.6 | 0.6 |
| 6-MNA | 93.5 | 64.0 | 0.7 |
| Etodolac | 60 | 74.4 | 1.2 |
| Salicyclic acid | >1000 | >1000 | −1 |

During the last decade several new selective COX-2 inhibitors and so called "preferential" COX-2 inhibitors have been identified. Several of these COX-2 inhibitors have been developed and a few of these have recently reached the market. Some of these new COX-2 inhibitors do not show inhibition of COX-1 in clinical doses. Extensive clinical studies and clinical practise on use of these COX-2 inhibitors show that these new COX-2 inhibitors have great advantages with regard to safety compared to non-selective NSAID's. For reviews on COX-2 inhibitors see for example Golden et al., 1999, Osteoarthritis. 25, p359-379, Mitchel et al., 1999, Brit. J. Pharmacol., 128, p1121-1132, Lipsky, 1999, Am. J. Med., 106 (5B), p515-575, Taketo, 1998, J. National Cancer Inst., 90, p1529-1537, Griswold et al., 1996, Med. Res. Rev., 16, p181-206 and Reitz et al., 1995, Ann. Rep. Med. Chem., 30, p179-188.

Further publications of interest on different COX-2 inhibitors include for example: Lane, 1997, J. Rheumatol., 24 (suppl. 49), p20-24, Mehlish et al., 1998, Clin. Pharmacol. Ther., 63, p1-8, Zhao et al., 1997, Arthritis Rheum., 40 (suppl.), S88, Ehrich et al., 1997, Arthritis Rheum., 40 (suppl.), S93, Maziasz et al., 1997, Arthritis Rheum., 40 (suppl.), S195, Mengle-Gaw et al., 1997, Arthritis Rheum., 40 (suppl.), S93, Morrison, 1999, Clin. Ther., 21, p943-953, Chan et al., 1995, J. Pharmacol. Exp. Ther., 274, p1531-37, Riendeau et al., 1997, Br. J. Pharmacol., 121, p105-117, Black et al., 1999, J. Med. Chem., 42, p1274-81, Cuo et al., 1996, J. Biol. Chem., 271, p19134-39, Geiss, 1999, Scand. J. Rheumatol., 109 (suppl.), p31-37, Warner et al., 1999, PNAS USA, 96, p7563-68, Bjarnson et al., 1997, Scand. J. Gastroenterol., 32, p126-130, Danneberg et al., 1999, Semin. Oncol., 26, p499-504, Mitchell et al., 1993, PNAS USA, 90, p11693-97, Futaki et al., 1994, Prostaglandins, 47, p55-9, Futaki et al., 1993, J. Pharm. Pharmacol., 45, p753-5, Masferrer et al., 1994, PNAS USA, 91, p3228-32, Klein et al., 1994, Biochem. Pharmacol., 48, p1605-10, Reitz et al., 1994, J. Med. Chem., 37, p3878-81, Seibert et al., 1994, PNAS USA, 91, p12013-17, Klein et al., 1996, Biochem. Pharmacol., 51, p285-90, Nantal et al., 1998, 9th Intern. Conference Inflamm. Res. Assoc., November 1-5, Pennig et al., 1997, J. Med. Chem., 40, p1347-65 and Puig et al., 2000, J. Med. Chem., 43, p214-223.

COX-2 inhibitors are a relatively diverse group of compounds from a chemical structure point of view. Compounds which selectively inhibit COX-2 are described in many patent documents of the last decade. Some of these are WO 94/26781, WO 94/20480, WO 94/13635, WO 95/00501, WO 94/27980, WO 94/15932, WO 95/21817, WO 95/15316, WO 96/06840, WO 96/03388, WO 96/03387, WO 96/03392, WO 96/25405, WO 96/24584, WO 96/03385, WO 96/16934, WO 98/41516, WO 98/43966, WO 99/12930, EPO 673 366, WO 98/41511, WO 98/47871, WO 99/20110, WO 99/23087, WO 99/14194, WO 99/14195, WO 99/15513 and WO 99/15503 and in U.S. Pat. Nos. 5,380,738, 5,344,991, 5,393,790, 5,434,178, 5,474,995, 5,475,018 and 5,510,368.

Two compounds are currently launched, rofecoxib (4-(4-methylsulfonyl)phenyl)-3-phenyl-2(5H)-furanone) (I) in Vioxx® and celecoxib (4-(5-(4-methylphenyl)-3-(trifluoromethyl)-1H-pyrazol-1-yl)-benzenesulfonamide) (II) in Celebra®:

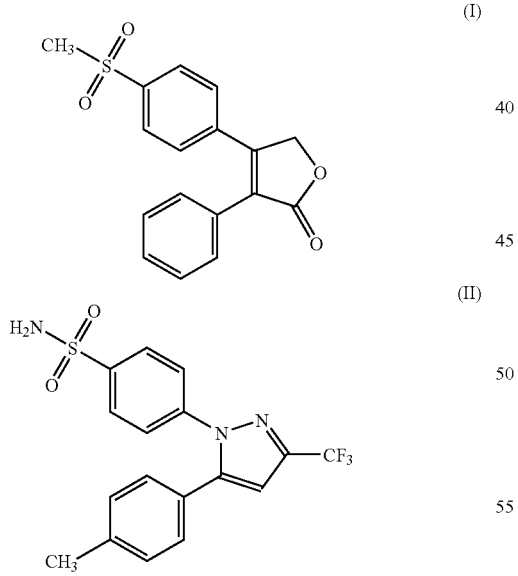

Rofecoxib is described in WO 93/0500501 from Merck Frosst Canada and further in Morrison, 1999, Clin. Ther., 21, p943-953, Chan et al., 1995, J. Pharmacol. Exp. Ther., 274, p1531-37 and in Nantel et al., 1998, supra.

Celecoxib is described by Geiss, 1999, Scand. J. Rheumatol., 109 (suppl.), p31-37 and by Penning et al., 1997, J. Med. Chem., 40, p1347-65. Celecoxib is described to be 375-fold more selective for COX-2 compared to COX-1.

Several other COX-2 inhibitors have been evaluated in biological systems and some of these are BF 389 (III), CGP 28232 (IV), DFP, DFU (V), DuP 697 (VI), etodolac (VII), FK 3311 (VIII), flosulide (IX), L-745,337 (X), meloxicam (Mobic®, U.S. Pat. No. 4,233,299, 4-hydroxy-2-methyl-N-(5-methyl-2-thiazolyl)-1,1-dioxide-2H-1,2-benzothiazine-3-carboxamide) (XI), MF tricyclic (XII), nimesulide (XIII), NS-398 (XIV) and SC-58125 (XV):

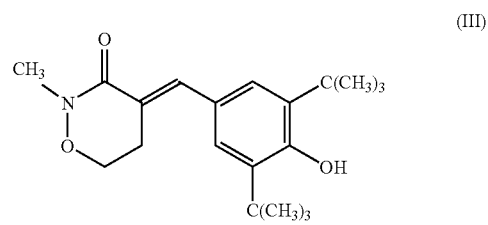

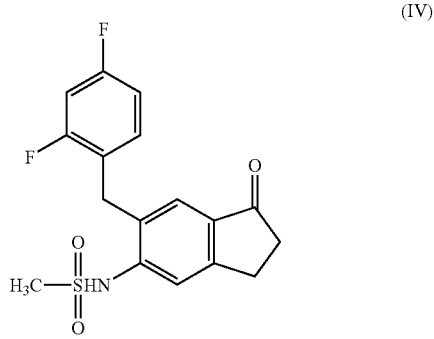

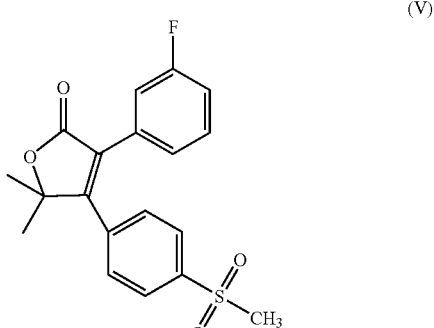

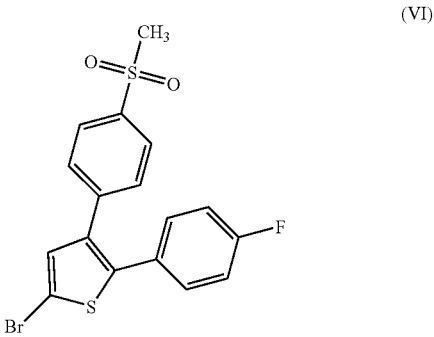

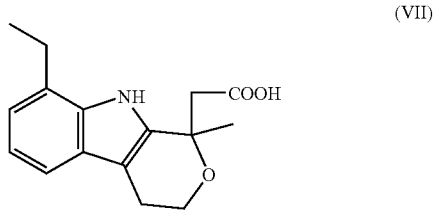

-continued

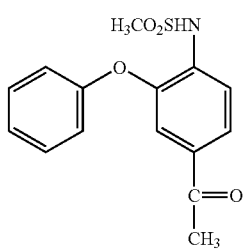
(VIII)

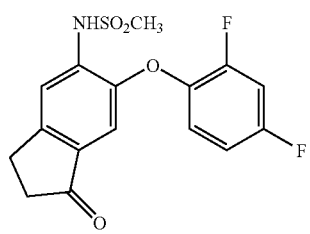
(IX)

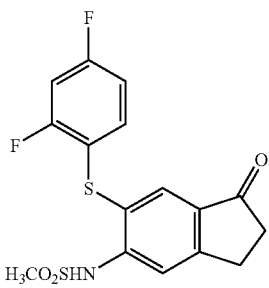
(X)

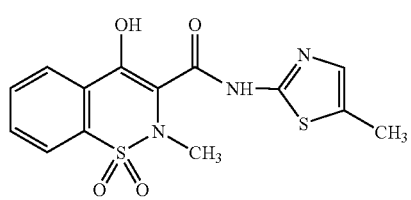
(XI)

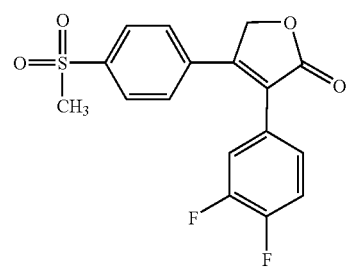
(XII)

(XIII)

-continued

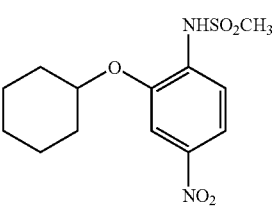
(XIV)

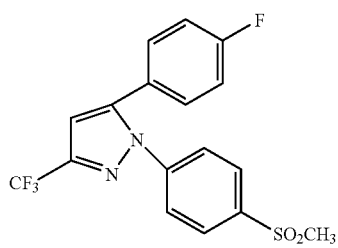
(XV)

Further compounds described for COX-2 inhibition include S-2474 (from Shionogi, EP 595546, 5(E)-(3,5-di-tert-butyl-4-hydroxy)benzylidene-2-ethyl-1,2-isothiazolidine-1,1-dioxide) (XVI), JTE-522 or RWK-57504 (4-(4-cyclohexyl-2-methyl-5-oxazolyl)-2-fluoro-benzenesulfonamide) (XVII), Darbufelone mesylate (Pfizer, WO 94/03448, monomethanesulfonate salt of 2-amino-5-((3,5-bis(1,1-dimethylethyl)-4-hydroxyphenyl)methylene-4(5H)-thiazolone) (XVIII), 6089 (from Kotobuki Pharmaceutical) (XIX), Valdecoxib (Pharmacia, 4-(5-methyl-3-phenyl-4-isoxazolyl)-benzenesulfonamide) (XX), Paracoxib sodium (Pharmacia, sodium salt of N-((4-(5-methyl-3-phenyl-4-isoxazolyl)-phenyl)sulfonyl)-propanamide) (XXI), 4-(2-oxo-3-phenyl-2,3-dihydrooxazol-4-yl)-benzenesulfonamide (Almirall-Prodespharma) (XXII) and Etoricoxib (MK-633, Merck and Co.):

(XVI)

(XII)

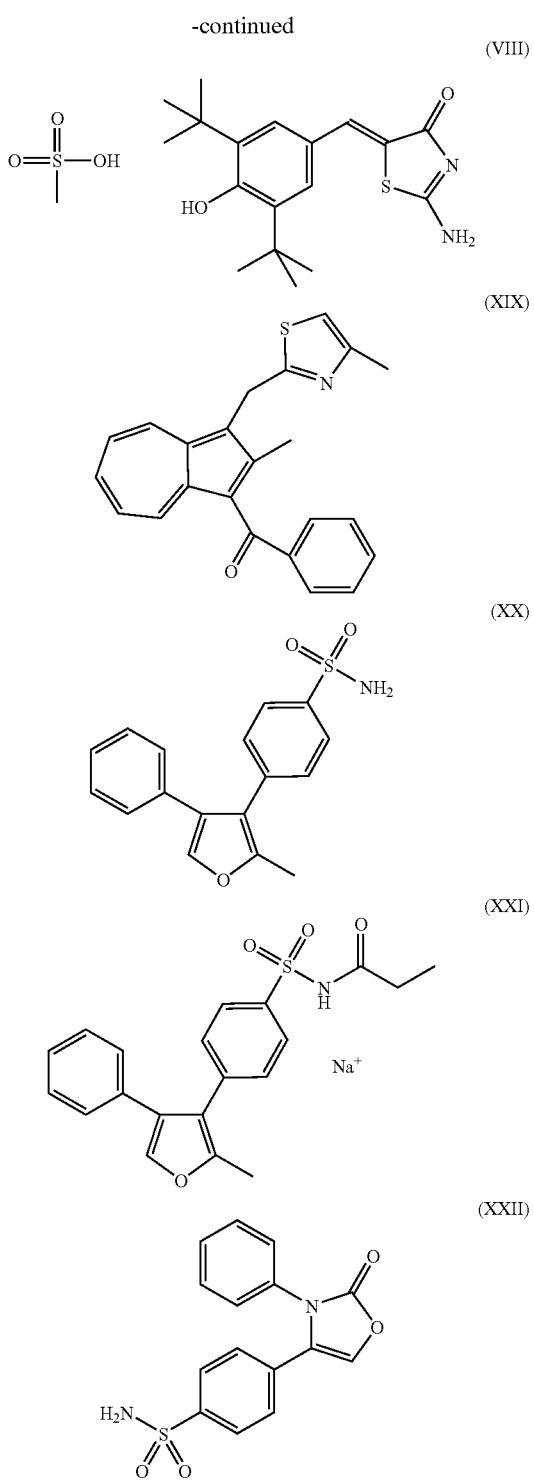

The above described compounds form preferred COX-2 inhibitors for use in the methods described hereinafter.

The indications for COX-2 inhibitors are arthritis, musculoskeletal pain conditions and general pain which have been treated with classical NSAIDs such as indomethacin, diclofenac and naproxen. Recently, it has also been suggested to use COX-2 inhibitors in cancer therapy and maybe also cancer prevention. COX-2 inhibitors might also have potential for use in relation to Alzheimer disease and other dementia-associated brain processes.

The potentials of the clinical utility of COX-2 inhibitors are discussed in for example Nature, 367, p215-216 (1994), in Drug News and Perspectives, 7, p501-512 (1994), in Annual Reports in Medicinal Chem., 30, p179-188 (1995) and in Oncogene, 18, p7908-7916 (1999).

There are no specific suggestions for use of COX-2 inhibitors in antiviral therapy or more specifically in HIV/AIDS therapy, and no COX-2 inhibitors have been tested with regard to anti-HIV effects. Furthermore, there is no suggestion to use COX-2 inhibitors (or non-selective COX-inhibitors) as immunostimulatory agents in the treatment of immunodeficiency of viral and non-viral origin.

HIV infection and AIDS is a major health problem with more than 33 million people infected with the virus worldwide. Most of the infected people are located in Africa (sub-Sahara) and in parts of Asia. There are today two classes of anti-AIDS compounds in routine clinical use; inhibitors of HIV reverse transcriptase and inhibitors of HIV protease. HIV reverse transcriptase inhibitors can be divided into non-nucleoside reverse transcriptase inhibitors (NNRTIs) and nucleoside reverse transcriptase inhibitors (NRTIs).

The most frequently used NNRTI's are nevirapine, delavirdine, efavirenz, emivirine and T180. The most frequently used NRTI's include zidovudine, didanosine, stavudine and zalcitabine. Clinically useful HIV protease inhibitors include inclinavir, palinavir and saquiravir.

The present treatment of HIV infection and AIDS is based on a combination of several drugs, a so-called cocktail of inhibitors of reverse transcriptase and protease inhibitors. These combinations, called HAART (highly active antiretroviral therapy), are quite effective and can reduce the virus back to undetectable levels in patient's blood. However, HAART is not a cure for the patient, because the virus is still present in the immune cells, and the disease can reappear at any time; upon discontinuation of therapy viremia peaks and rapid progression to AIDS is frequently observed. Furthermore, the immunodeficiency and the HIV-specific T-cell dysfunction persists during HAART. This therapy requires life-long treatment and the treatment is very expensive. The cost of the drugs alone, often exceeds USD 15 000. There are, in addition, several other problems associated with this therapy; difficulties with patient compliance (complicated drug regimes), development of resistant viruses, non-ideal pharmacokinetics and side effects such as, for example, suppression of bone-marrow and long-term metabolic effects.

For recently published reviews on anti-HIV therapy see for example: Hilgegroth, 1998, Pharm. uns. Zeit., 1998, 27, p22-25, Hilgegroth, 1998, Pharm. uns Zeit., 7, p111-116, Stellbrink, 1997, Dk Ärztebl., 94, p2497-2503, Rettle et al., 1998, Int. J. STD AIDS, 9, p80-87, De-Clercq, 1998, Antiviral Res., 38, p153-179, Gait et al., 1995, TIBTECH, 13, p430-438 and Redshaw et al. in "Emerging Drugs: The Prospects of Improved Medicines", Chapter 6, p127-154, 1997.

In conclusion, although multidrug combinations like HAART has significantly improved the prognosis for patients suffering from HIV infection, there is a medical need for new compounds in antiviral therapy of HIV; especially agents stimulating the immune system. The present invention addresses this need.

Expression of COX-2 is normally restricted to brain/brain processes, to arthritic synovia and sites of tissue injury. COX-2 is not found in normal lymph nodes or lymphocytes. It has now surprisingly been found however that in mice infected by the immunodeficiency disorder MAIDs, lymph node cells express high levels of COX-2. Furthermore, positively selected CD4+ and CD8+ T cells as well as B cells from MAIDS lymph nodes contained high levels of COX-2 (see Example 2). It has been found that this COX-2 may be targetted to alleviate symptoms of the immunodeficiency disorder, e.g. to alleviate T cell dysfunction by acting as an immunostimulant, e.g. by generating antigen-specific immune responses.

Whilst not wishing to be bound by theory, it is believed that COX-2 activity increases $PGE_2$ production which in turn increases the levels of cAMP which activates the PKA signalling pathway resulting in impaired lymphocyte function. Work conducted on mice with MAIDs in vivo illustrates that COX-2 inhibitors improve the immune functions of T cells (see Example 6).

The present invention provides a new method for treating or preventing immunodeficiency; especially for treatment of HIV and AIDS which comprises treating a subject with a therapeutically effective amount of a COX-2 inhibitor or derivative or pharmaceutically acceptable salt thereof.

Thus in a first aspect the present invention provides a method of treating or preventing a disorder typified by increased COX-2 activity, such as disorders typified by decreased immune function, in a human or non-human animal (e.g. through increased COX-2 expression) wherein said animal is administered a therapeutically effective amount of a COX-2 inhibitor or derivative or pharmaceutically acceptable salt thereof.

As used herein increased COX-2 activity refers to increased levels of activity either through the production of more COX-2 molecules (e.g. increased expression), and/or more active molecules (e.g. conversion from latent to active forms or removal of inhibition of the active form). Preferably said disorder is typified by decreased immune function, ie. is a condition of immunodeficiency e.g. exhibits lymphocyte dysfunctions. As used herein "immunodeficiency" refers to impaired function of cells involved in normal immune responses, particularly B and T cells. Thus compounds described herein may be used to achieve immunostimulatory effects to enhance immune responses. Thus COX-2 inhibitors are considered to have immunomodulatory effects. Preferably conditions which may be treated include virally-induced immunodeficiency disorders.

Thus, the method above would be useful for, but not limited to, the treatment of HIV or AIDS related disorders in a subject. For example, approximately 50% of patients with common variable immunodeficiency have a T-cell dysfunction similar to that of HIV infection and could benefit from immunostimulatory treatment. According to the present invention, any COX-2 inhibitor may be administered to a subject in need of HIV/AIDS therapy. Thus preferred conditions for treatment according to the invention include infection by retroviruses, particularly HIV (and infection by related viruses in other animals, e.g. SIV, FIV, MAIDS) and the resultant AIDS and treatment of common variable immunodeficiency and related conditions to the aforementioned conditions.

Subjects which may be treated are preferably mammalian, preferably humans and companion or agricultural animals such as dogs, cats, monkeys, horses, sheep, goats, cows, rabbits, rats and mice.

Alternatively stated, the present invention provides a COX-2 inhibitor or derivative or pharmaceutically acceptable salt thereof for treating or preventing a disorder typified by increased COX-2 activity as described above or the use of a COX-2 inhibitor or derivative or pharmaceutically acceptable salt thereof in the preparation of a medicament for treating or preventing a disorder typified by increased COX-2 activity as described above. As used herein "treating" refers to the reduction or alleviation, preferably to normal levels, of one or more of the symptoms of said disorder, e.g. infectivity or a reduction or alleviation of immune dysfunction. "Preventing" refers to absolute prevention, i.e. absence of detectable infectious agent, e.g virus and/or maintenance of normal levels with reference to a particular symptom (e.g. COX-2 activity) or reduction or alleviation of the extent or timing (e.g. delaying) of the onset of that symptom.

The enzyme cyclooxygenase 2 is a new target for HIV/AIDS therapy. The term "COX-2 inhibitor" denotes a compound able to inhibit the enzyme cyclooxygenase 2 without significant inhibition of cyclooxygenase 1 when administered at a particular concentration. Preferably, it includes compounds having a selectivity for cyclooxygenase-2 inhibition relative to cyclooxygenase-1 inhibition (e.g. as determined by the COX-1:COX-2 $IC_{80}$ ratio according to the WHMA test, see below) of at least 10, more preferably of at least 50, and even more preferably of at least 100. (The selectivity ratio for one specific compound will vary with the biological assay and the form in which it is expressed (preferably expressed as the ratio of COX-1:COX-2 $IC_{50}$ or $IC_{80}$), see tables 1-4). The ratios described here refer to data obtained in one or more relevant, well known COX assays, preferably using purified human enzymes, e.g. ratio of $IC_{50}$ values for example as determined by Engelhart et al., 1995, supra. Preferably however, the test is the WHMA test as described below.

A number of analyses of relative potencies of COX-1 and COX-2 have been performed using a wide range of assay systems from isolated purified enzymes to intact cells and cell models from various species. However, at present, the most widely accepted model is the human whole blood assay (WBA) and a modified version William Harvey human modified whole blood assay (WHMA) which is the preferred assay. These assays make use of readily available human cells for testing which is preferable for human use of the compounds. It also takes into account the binding of NSAids to plasma proteins. Furthermore, assessment of selectivity is preferably made at $IC_{80}$ rather than at $IC_{50}$ as the concentration curves for inhibition of COX-2 and COX-1 are not parallel and since most compounds are used at doses giving steady-state plasma concentrations of closer to 80% inhibition (Warner et al., 1999, PNAS USA, 96, p7563-7568)

In the WBA assay, for COX-1 analysis blood is treated with test agent followed 60 min later by calcium ionophore and incubated for 30 min after which plasma is collected. For COX-2 analysis, blood is treated with aspirin to inhibit COX-1 and 6 hours later with lipopolysaccharide and test agent and incubated for 18 hours after which plasma is collected. Subsequently, the content of thromboxane B2 in plasma is assessed by radioimmunoassay as a measure of COX activity.

In the WHMA assay, COX-1 analysis is conducted as above. For COX-2 analysis, blood is treated with conditioned medium from cultures of human airway epithelium cells (A549) exposed to interleukin 1β for 24 hours and incubated with this medium together with test agent for 60 min after which calcium ionophore is added followed 30 min later by diclofenac to stop production of prosanoids. Subsequently, plasma is collected and analysed for its content of prostaglandin E2 in plasma by radioimmunoassay as a measure of COX-2 activity. The times of incubation for assessment of COX-1 and COX-2 activities are similar in this last assay which makes activities more comparable and the WHMA the preferred assay.

Using this assay, selectivity based on COX-2/WHMA-COX-1 at $IC_{80}$ is shown in Table 4 where 0.2 and 0.02 represents 5- and 50-fold selectivities for COX-2, respectively.

TABLE 4

(Ratio COX-2/COX-1 at $IC_{80}$ according to the WHMA test taken from Warner, et al., supra):

| Compound | Ratio COX-2/WHMA-COX-1 at $IC_{80}$ |
|---|---|
| Diisopropylfluorophosphate | <0.01 |
| L-745337 | <0.01 |
| rofecoxib | 0.015 |
| NS398 | <0.05 |
| SC58125 | <0.01 (WBA assay) |
| etodolac | 0.043 |
| meloxicam | 0.091 |
| celecoxib | 0.11 |
| nimesulide | 0.17 |

In a preferred feature therefore the selectivity ratio is determined according to the WHMA assay at $IC_{80}$ and compounds having a selectivity ratio of COX-2:COX-1 of less than 0.2, preferably less than 0.05, e.g. less than 0.02, preferably less than 0.01, e.g. <0.005 are particularly preferred for use in methods of the invention. Alternatively stated, preferred compounds have a COX-1:COX-2 selectivity ratio (according to the WHMA assay at $IC_{80}$) of more than 2, preferably more than 5, especially preferably more than 50 or 100, as mentioned previously.

"Inhibition" as referred to herein refers to a reduction in measurable cyclooxygenase-2 activity. This may be achieved by affecting transcription, translation, post-translational modification or activity of COX-2. Preferably however inhibition is achieved by inhibiting the enzymatic activity, i.e. interfering with the active site of pre-existing active COX-2 molecules.

Preferably, COX-2 inhibitors for treatment of immunodeficiency or viral infection, especially HIV infections and AIDS, have a COX-2 $IC_{50}$ of less than about 0.5 µmol/liter, more preferably less than about 0.2 µmol/liter.

The method provided herein relates to the use of COX-2 inhibitors or derivatives thereof in the prevention and treatment of various conditions, including immuno-deficiencies and viral infections; especially HIV and AIDS.

In one preferred embodiment of the present invention, the COX-2 inhibitor for treatment according to the invention is selected from acidic sulfonamides.

In one preferred embodiment, COX-2 inhibitors for use in the invention are selected from the compounds according to the general formula A below including methansulphonamide ethers and thioethers:

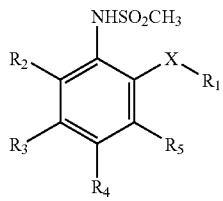

A wherein
X represents an oxygen or sulphur atom or alkyl group, preferably a —$CH_2$— group;
$R_1$ represents a cycloalkyl or aryl group which may optionally be substituted by one or more groups or atoms, preferably by one or more halogen atoms, such as fluorine;
$R_2$, $R_3$, $R_4$ and $R_5$ independently represent a hydrogen atom, a nitro or acyl group or an alkyl group which may optionally be substituted by one or more groups (e.g. an acyl group) or atoms or alternatively $R_2$ and $R_3$, $R_3$ and $R_4$ or $R_4$ and $R_5$ together with the intervening carbon atoms form a cyclopentanone group;

or a derivative or a pharmaceutically acceptable salt thereof.

Preferably in such compounds X is an oxygen atom. In further preferred compounds $R_1$ is an aryl group or an aryl group substituted with one or more fluorine atoms, or a cycloalkyl group.

In further preferred compounds $R_2$ and $R_3$ are hydrogen atoms and $R_4$ is an —$NO_2$ or —$COCH_3$ group. Alternative preferred compounds comprise those in which $R_2$ is a hydrogen atom and $R_3$ and $R_4$ together form a cyclopentanone group.

Especially preferred compounds of formula A for use in the invention are compounds described herein denoted flosulide, NS-398, nimesulide, FK 3311, CGP 28232 and L-745 337.

In another preferred embodiment of the present invention, the COX-2 inhibitor for use in the invention is selected from diaryl heterocycles.

One example of a family of diaryl heterocycles which may be used as COX-2 inhibitors for use in the invention comprises compounds of the general formula B below

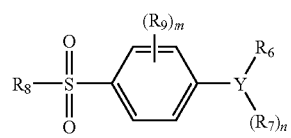

B wherein
Y represents a cyclic group, preferably selected from oxazolyl, isoxazolyl, thienyl, dihydrofuryl, furyl, pyrrolyl, pyrazolyl, thiazolyl, imidazolyl, isothiazolyl, cyclopentenyl, phenyl and pyridyl;
n is an integer from 0 to 3;
m is an integer from 0 to 4;
$R_6$ represents a ketocyclyl, cycloalkyl or aryl group, which group may optionally be substituted by one or more groups or atoms, preferably by one or more halogen atoms, such as fluorine;
$R_7$ each independently represent a substituent which may be any functional group, preferably a hydrogen or halogen atom, preferably fluorine or bromine, or an alkyl group (preferably —$CH_3$), which alkyl group may be substituted by one or more groups or atoms, preferably one or more fluorine atoms for example —$CF_3$;
$R_8$ represents an alkyl group, preferably —$CH_3$ or $NHR_{10}$, preferably —$NH_2$;
$R_9$ represents a halogen atom, preferably fluorine; and
$R_{10}$ represents a hydrogen atom or an alkyl group optionally substituted by one or more groups or atoms, preferably by an acyl group;

or a derivative or a pharmaceutically acceptable salt thereof.

This class of compounds is claimed as anti-angiogenic agents in U.S. Pat. No. 6,025,353 and a further description of preferred substituents and compounds according to the present invention are the same as in U.S. Pat. No. 6,025,353.

Preferably in such compounds $R_8$ is —$NH_2$ or —$CH_3$. In further preferred compounds Y is a pyrazolyl, furyl or thienyl group. Preferably $R_6$ is an aryl group optionally substituted with one or more fluorine atoms. Preferably n is 1 or 2. Preferably $R_7$ is a bromine atom, an acyl group or a substituted alkyl group such as —$CF_3$.

Especially preferred compounds of formula B for use in the invention are compounds described herein denoted celecoxib, rofecoxib, DuP-697, SC-58125, DFP, DFU and MF tricyclic.

As used herein, the term "alkyl" includes any long or short chain, straight-chained, branched or cyclic aliphatic saturated or unsaturated hydrocarbon group optionally mono or poly substituted by hydroxy, alkoxy, acyloxy, nitro, alkoxycarbonyloxy, amino, aryl, oxo or halo groups unless specifically stated otherwise. The unsaturated alkyl groups may be mono- or polyunsaturated and include both alkenyl and alkynyl groups. Such groups may contain up to 40, but preferably 1 to 10 carbon atoms.

As used herein cyclic rings are preferably $C_{5-7}$ and optionally contain one or more heteroatoms selected from oxygen, nitrogen and sulphur.

The term "acyl" as used herein includes both carboxylate and carbonate groups, thus, for example, acyloxy substituted alkyl groups include for example alkylcarbonyloxy alkyl. In such groups any alkylene moieties preferably have carbon atom contents defined for alkyl groups above. Preferred aryl groups include phenyl and monocyclic 5-7 membered heteroaromatics, especially phenyl and such groups may themselves optionally be substituted.

Representative substituted alkyl groups $R_1$ include alkoxyalkyl, hydroxyalkoxyalkyl, polyhydroxyalkyl, hydroxy poly alkyleneoxyalkyl and the like such as alkoxymethyl, alkoxyethyl and alkoxypropyl groups or acyloxymethyl, acyloxyethyl and acyloxypropyl groups eg. pivaloyloxymethyl.

As used herein substituted groups may be mono or poly substituted by hydroxy, alkoxy, acyloxy, nitro, alkoxycarbonyloxy, amino, aryl, oxo or halo groups unless specifically stated otherwise.

In another preferred embodiment of the present invention, the COX-2 inhibitor is selected from modifications of classical NSAID's, for example the pro-drugs, esters or salts thereof.

With basis in the chemical structures of classical NSAIDs, more new selective COX-2 inhibitors have been prepared. Such a compound may be meloxicam which is an oxecam (the COX-2 specific analogue of the well known piroxicam), or acetic acid derivatives such as etodolac (COX-2 specific analogue of diclofenac). Other examples of some of the most preferred compounds in this class are COX-2 active indomethacin derivatives and zomepirac.

A further listing of families and subfamilies of compounds according to the present invention is found in patents and patent applications on COX-2 inhibitors; for example in the patent documents previously listed in this text. These patent documents also exemplify and list specific compounds that also are the most preferred COX-2 inhibitors according to the invention.

Particularly preferred compounds are however: diisopropylfluorophosphate, L-745337, rofecoxib, NS 398, SC 58125, etodolac, meloxicam, celecoxib and nimesulide.

Methods for producing COX-2 inhibitors for use in accordance with the invention are well known to those in the art, particularly as described in the literature mentioned above.

A COX-2 inhibitor for use in treatment and prevention of disorders as described herein, e.g. immunodeficiencies and viral infections, especially HIV/AIDS, according to the present invention may contain one or more asymmetric centres and/or one or more double bonds i.e. the invention extends to use of isomers and racemates of the compounds disclosed herein. All such possible isomers are within the scope of the present invention. The COX-2 inhibitor can be in the form of an isomeric mixture of compounds or more preferably in the form of a purified isomer or a pharmaceutically acceptable salt thereof.

The pharmaceutical composition of COX-2 inhibitor(s) for treatment of conditions according to the invention, e.g. immunodeficiencies and viral infections can be formulated as pharmaceutically acceptable salts and can also contain pharmaceutically acceptable carriers well known in the art.

Thus, the present invention also extends to pharmaceutical compositions comprising a COX-2 inhibitor or derivative or pharmaceutically acceptable salt thereof and a pharmaceutically acceptable diluent, carrier or excipient. By "pharmaceutically acceptable" is meant that the ingredient must be compatible with other ingredients in the composition as well as physiologically acceptable to the recipient.

In further embodiments the present invention also extends to the use of such compositions and methods of prevention/treatment using such compositions, as described hereinbefore.

If the COX-2 inhibitor is basic, salts can be prepared from pharmaceutically acceptable non-toxic acids including inorganic and organic acids. Particularly preferred salts are hydrochloric, hydrobromic, phosphoric, sulfuric, citric, maleic, citric and tartaric acid salts.

If the COX-2 inhibitor is acidic, salts can be prepared from pharmaceutically acceptable non-toxic bases including inorganic or organic bases. Particularly preferred salts are sodium, potassium and meglumine salts.

For the treatment and prevention of disorders as described herein, e.g. immunodeficiency or viral diseases including HIV/AIDS, the COX-2 inhibitors can be administered orally, rectally, topically, buccally, by inhalation or parenterally (e.g. intramuscularly, subcutaneously, intraperitoneally or intravenously) in the form of an injection or infusion. The preferred administration forms will be administered orally, rectally and by injection or infusion. The most preferred administration form will be suitable for oral administration.

For all administration forms, the COX-2 inhibitor is administered in dosage unit formulations usually containing well known pharmaceutically acceptable carriers, adjuvants and vehicles. Thus, the active ingredient may be incorporated, optionally together with other active substances as a combined preparation, with one or more conventional carriers, diluents and/or excipients, to produce conventional galenic preparations such as tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavouring agents, adsorption enhancers, e.g. for nasal delivery (bile salts, lecithins, surfactants, fatty acids, chelators) and the like. The compositions of the invention may be formulated so as to provide quick, sustained or delayed release of the active ingredient after administration of the patient by employing procedures well known in the art.

The active ingredient for administration may be appropriately modified for use in a pharmaceutical composition. For example, the active ingredient may be stabilized for example by the use of appropriate additives such as salts or non-electrolytes, acetate, SDS, EDTA, citrate or acetate buffers, mannitol, glycine, HSA or polysorbate.

Conjugates may be formulated to provide improved lipophilicity, increase cellular transport, increase solubility or allow targeting. These conjugates may be cleavable such that the conjugate behaves as a pro-drug. Stability may also be conferred by use of appropriate metal complexes, e.g. with Zn, Ca or Fe.

The active ingredient may be formulated in an appropriate vehicle for delivery or for targeting particular cells, organs or tissues. Thus the pharmaceutical compositions may take the form of microemulsions, liposomes, niosomes or nanoparticles with which the active ingredient may be absorbed, adsorbed, incorporated or bound. This can effectively convert the product to an insoluble form.

These particles may carry appropriate surface molecules to improve circulation time (e.g. serum components, surfactants, polyoxamine908, PEG etc.) or moieties for site-specific targeting, such as ligands to particular cell borne receptors. Appropriate techniques for drug delivery and for targeting are well known in the art, but see for example Kreuter, 1994, Eur. J. Drug Metab. Pharmacokinet., 3, p253-256; Shen, 1997, J. Drug Targeting, 5(1), p11-13; Mrsny, 1997, J. Drug Targeting, 5(1), p5-9; Pettit & Gombotz, 1998, TIBTECH, 16, p343-349; and Duncan, 1997, J. Drug Targeting, 5(1), p1-4 regarding drug targeting and Simari & Nabel, 1996, Semin. Intervent. Cardiol., 1, p77-83; Torchilin, 1998, J. Microencapsulation, 15(1), p1-19; Klyashchitsky & Owen, 1998, J. Drug Targeting, 5(6), p443-458; Kreuter, 1996, J. Anat., 189, p503-505; Fasano, 1998, TIBTECH, 16, p152-157; Kataoka et al., 1993, 24, p119-132; Anderson, 1998, Nature, 392 (suppl), p25-30; Langer, 1998, Nature, 392(suppl), p5-10; Gregoriadis, 1995, TIBTECH, 13, p527-536; Gregoriadis et al., 1997, FEBS Lett., 402, p107-110; Rolland, 1998, Critical Reviews in Therapeutic Drug Carrier Systems, 15(2), p143-198; Hope et al., 1998, Molec. Memb. Biol., 15, p1-14; and Scherman et al., 1998, Curr. Opinion Biotech., 9(5), p480-485 regarding peptide and nucleic acid molecule delivery. For an example of specific site directed targeting, see for example Schäfer et al., 1992, Pharm. Res., 9, p541-546 in which nanoparticles can be accumulated in HIV-infected macrophages. Clearly such methods have particular applications in the methods of the invention described herein.

Such derivatized or conjugated active ingredients are intended to fall within the definition of inhibitory molecules which are used according to the invention.

Thus for example, the pharmaceutical composition for oral use contains the active ingredient(s) and suitable physiologically acceptable agents to form tablets, capsules, solutions, suspensions or other well known formulations for oral administration. Such compositions can be prepared according to any method known for the manufacture of oral pharmaceutical compositions. Such compositions can contain one or more biologically active agents and one or more agents selected from the group of preserving agents, inert diluents, viscosity increasing agents, colouring agents, sweetening agents, granulating agents, disintegrating agents, binding agents, osmotic active agents, wetting agents, suspending agents, materials for preparation of delay formulations, oils and water.

Pharmaceutical compositions for other than oral use, for example suppositories for rectal administration or solutions for injections or infusions can be prepared using well known methods and additives for such formulations. All formulations for injection and infusion should be sterile formulations.

The active ingredient in such compositions may comprise from about 0.01% to about 99% by weight of the formulation, preferably from about 0.1 to about 50%, for example 10%.

For treatment of disorders in accordance with the invention, e.g. immunodeficiencies and viral infections, with COX-2 inhibitors, the dose levels per day are in the range 0.005 mg to about 150 mg/kg of body weight. The dose depends strongly on the choice of the COX-2 inhibitor compound, the clinical situation (type of virus, status of the infection and condition of the patient), the patient's age and weight, route of administration and the total use of drugs by the patient including the length of the course of treatment. More preferred doses will normally be between 0.01 mg and 50 mg/kg of body weight daily, and even more preferably 0.05 mg to 20 mg/kg of body weight daily. Thus for example, 25 mg of rofecoxib or 200 mg celecoxib may be administered daily by oral administration to an adult human.

Dosage units are generally between 1 mg and 500 mg of the active ingredient.

According to one aspect of the present invention, one COX-2 inhibitor can be combined with one or more other COX-2 inhibitors to treat disorders as described herein, e.g. an immunodeficiency or viral infection.

According to another aspect of the present invention, the COX-2 inhibitor can be combined with one or more further COX-2 inhibitors or one or more other drugs with different modes of action to treat the disorder, e.g. the immunodeficiency, HIV infection, or AIDS. Examples of such combinations could be COX-2 inhibitor in combination with one or more NNRTIs or in combination with one or more NRTIs or in combination with one or more HIV protease inhibitors or one or more HAART in combination with the COX-2 inhibitor.

In a further aspect the present invention provides methods and/or compositions which combine one or more COX-2 inhibitors with compounds that improve the tolerability of the active ingredient, especially during long term treatment. Typical compounds include antihistamine and proton pump inhibitors.

Thus the invention extends to a composition comprising a COX-2 inhibitor as described hereinbefore together with one or more additional COX-2 inhibitors and/or one or more additional active ingredients. The invention further extends to use of such compositions and methods of using such compositions as described hereinbefore. The invention further extends to a product comprising the components described above as a combined preparation for simultaneous, separate or sequential use in treating or preventing conditions or disorders as described hereinbefore.

Figure 2:
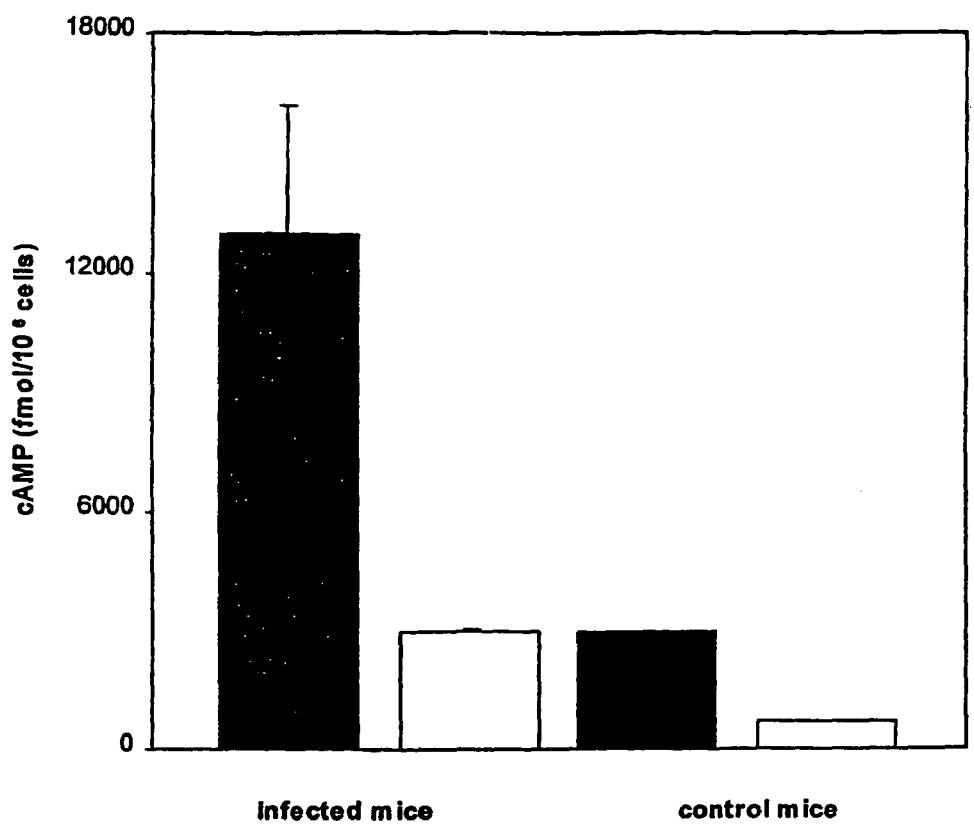
Figure 3:
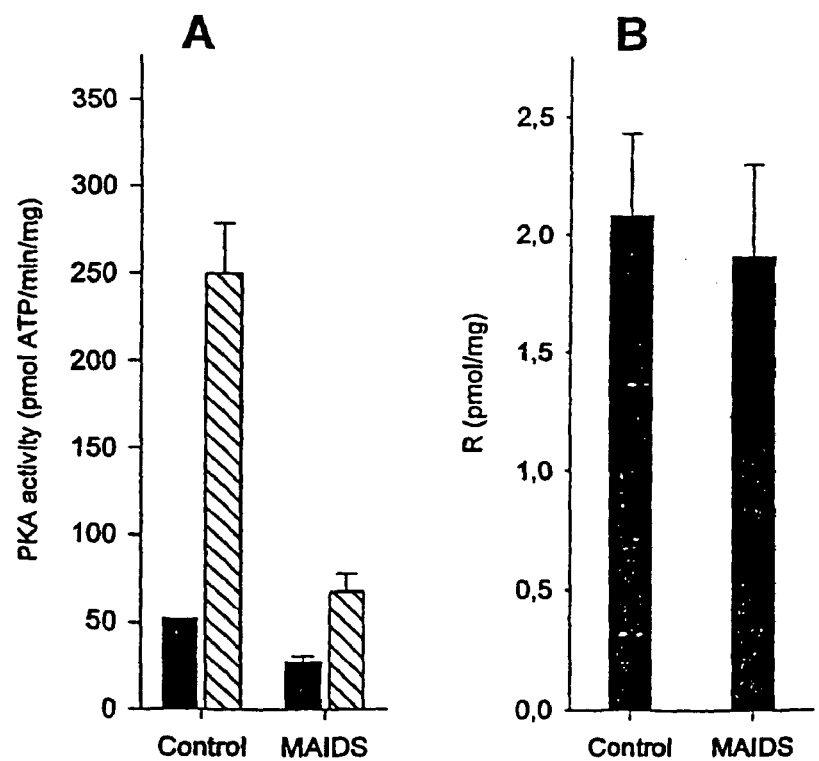
Figure 4:
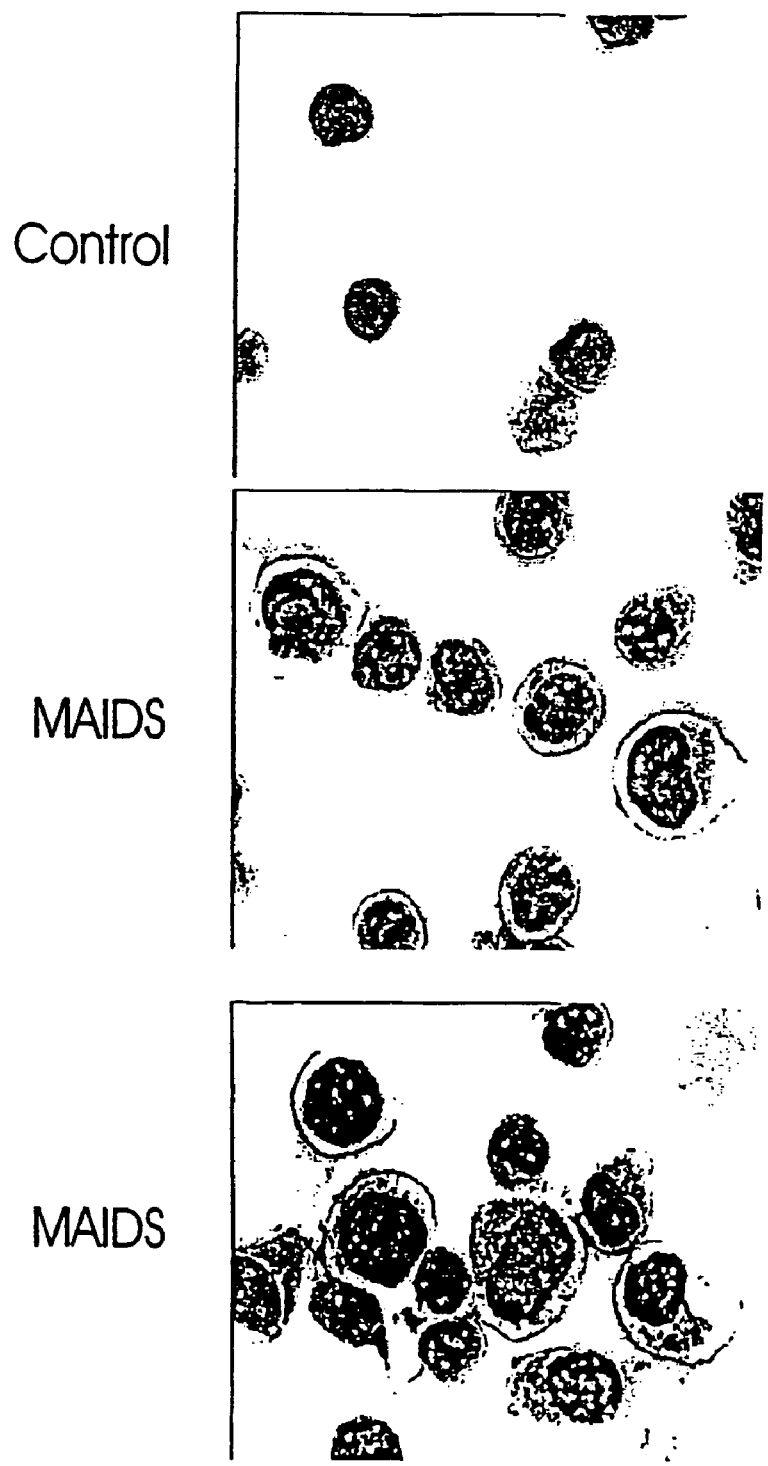
Figure 5:
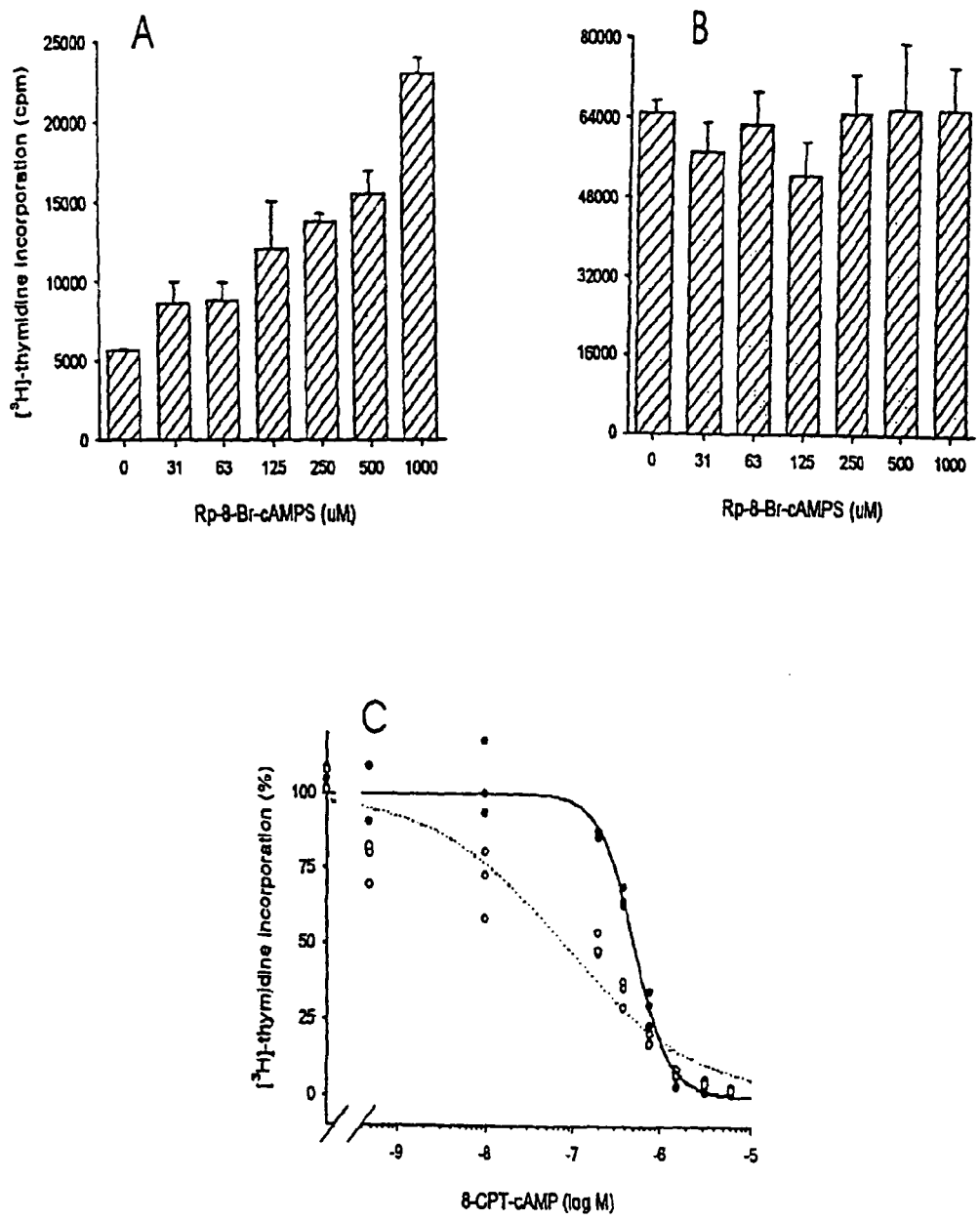
Figure 6:
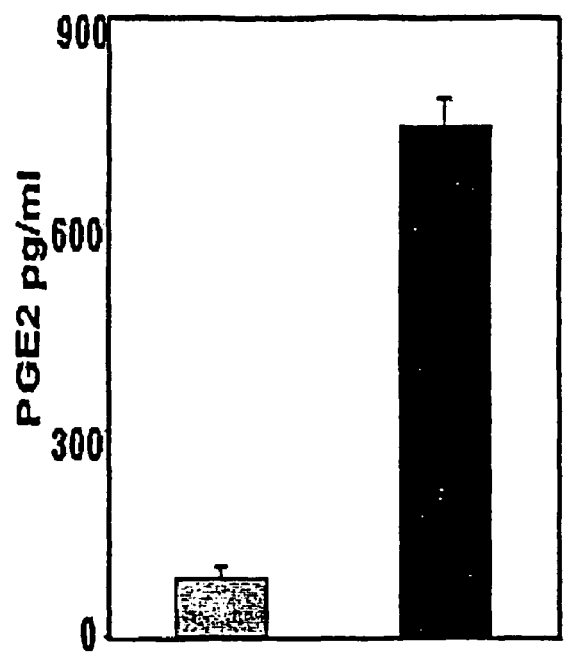
Figure 7:
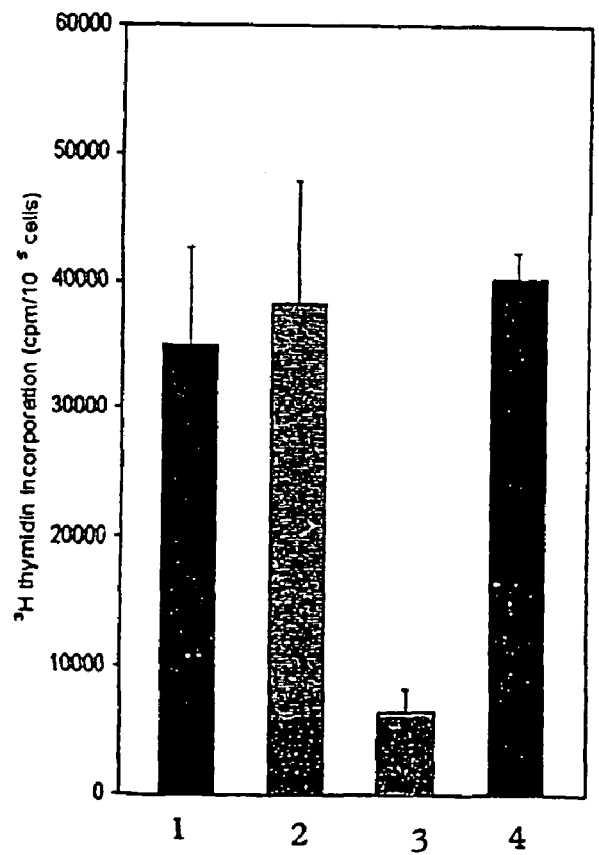
Figure 8:
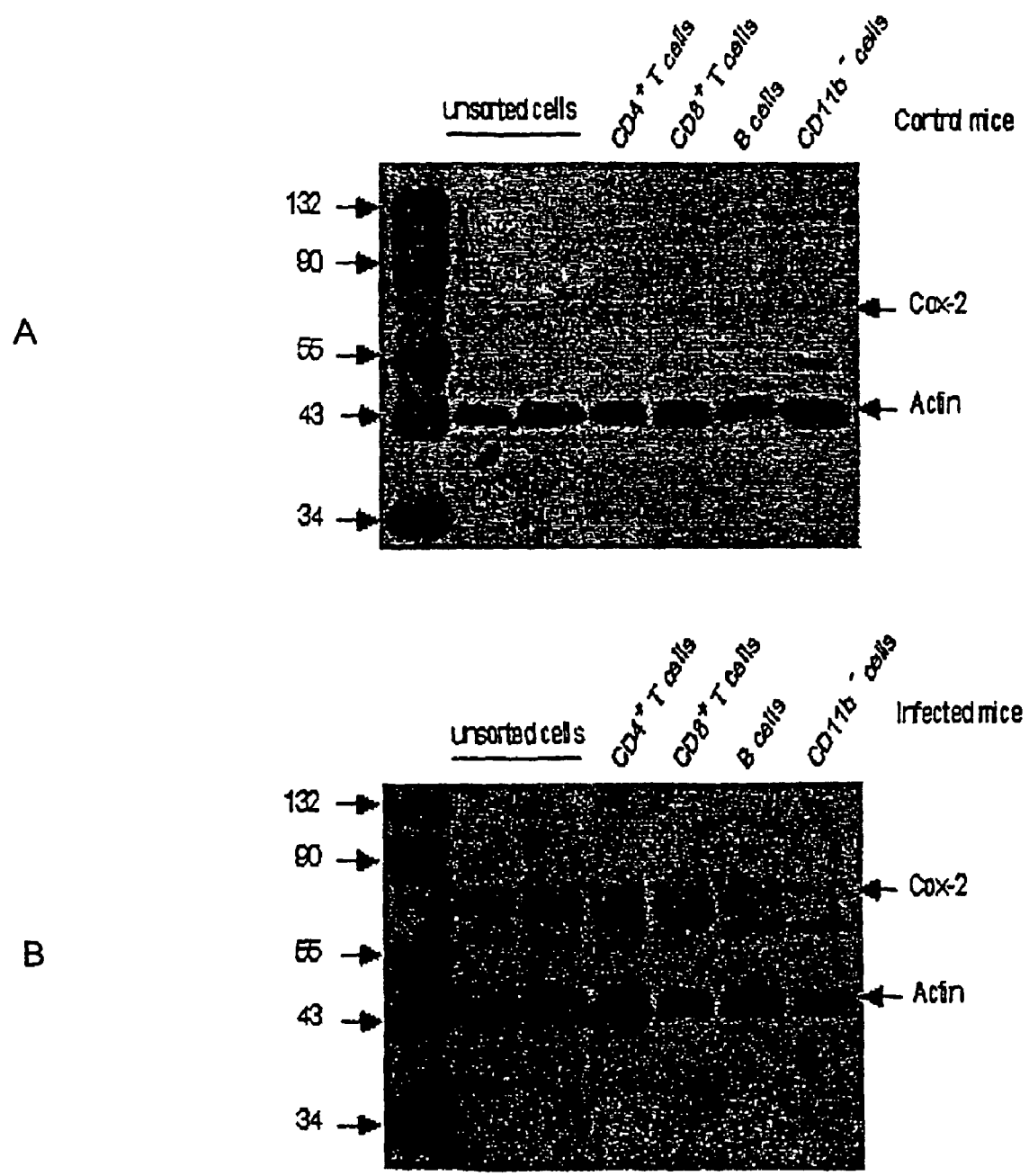
Figure 9:
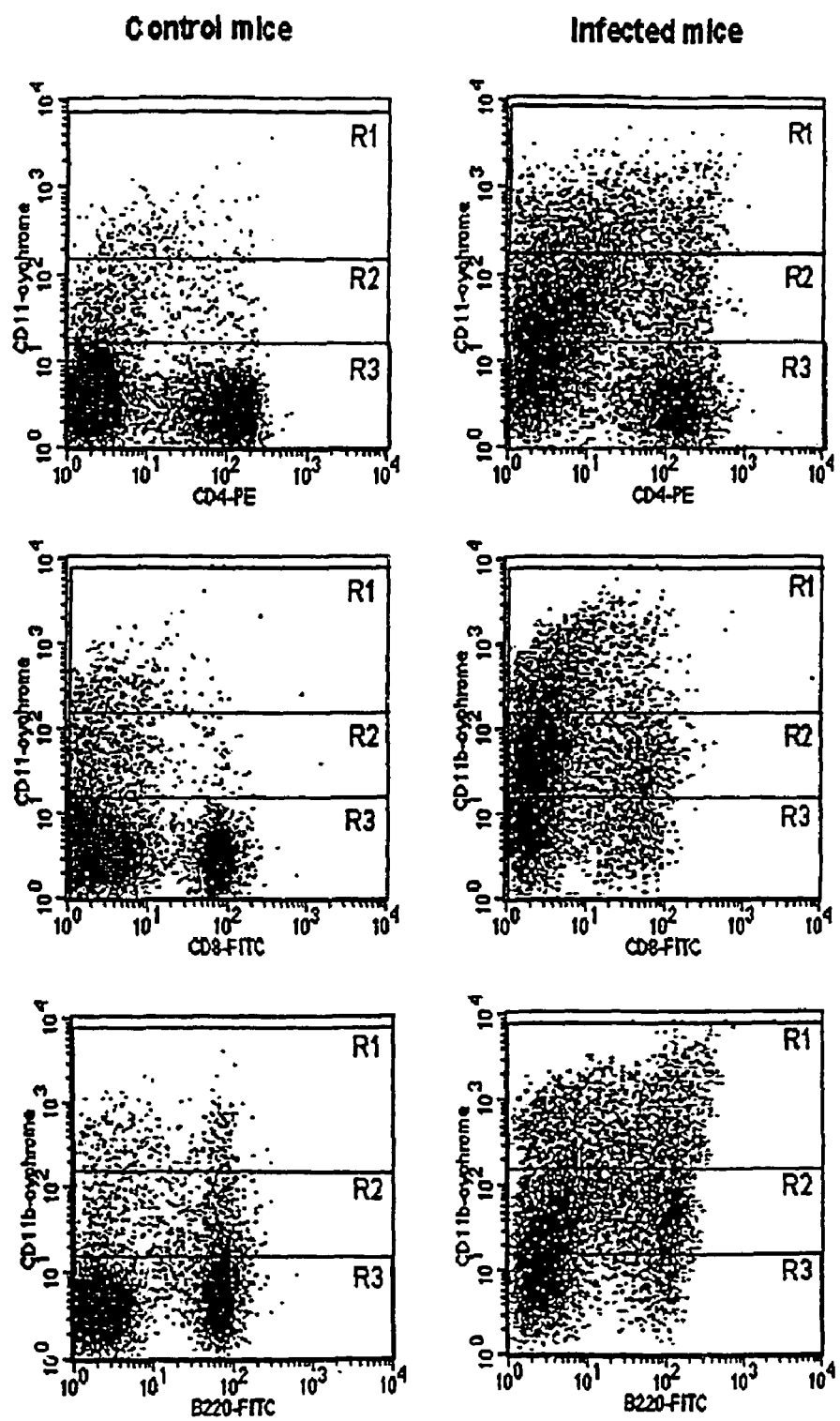
Figure 10:
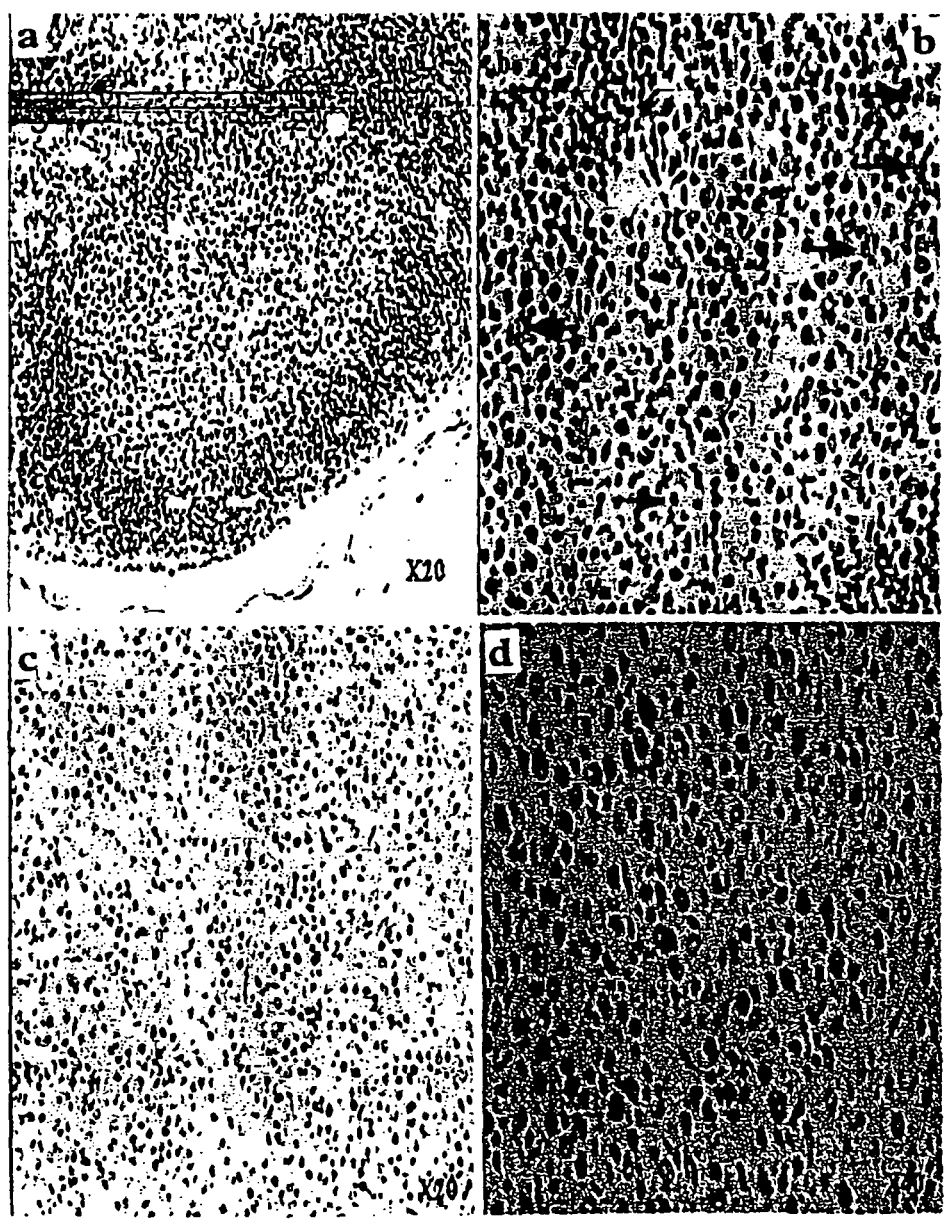
Figure 11:
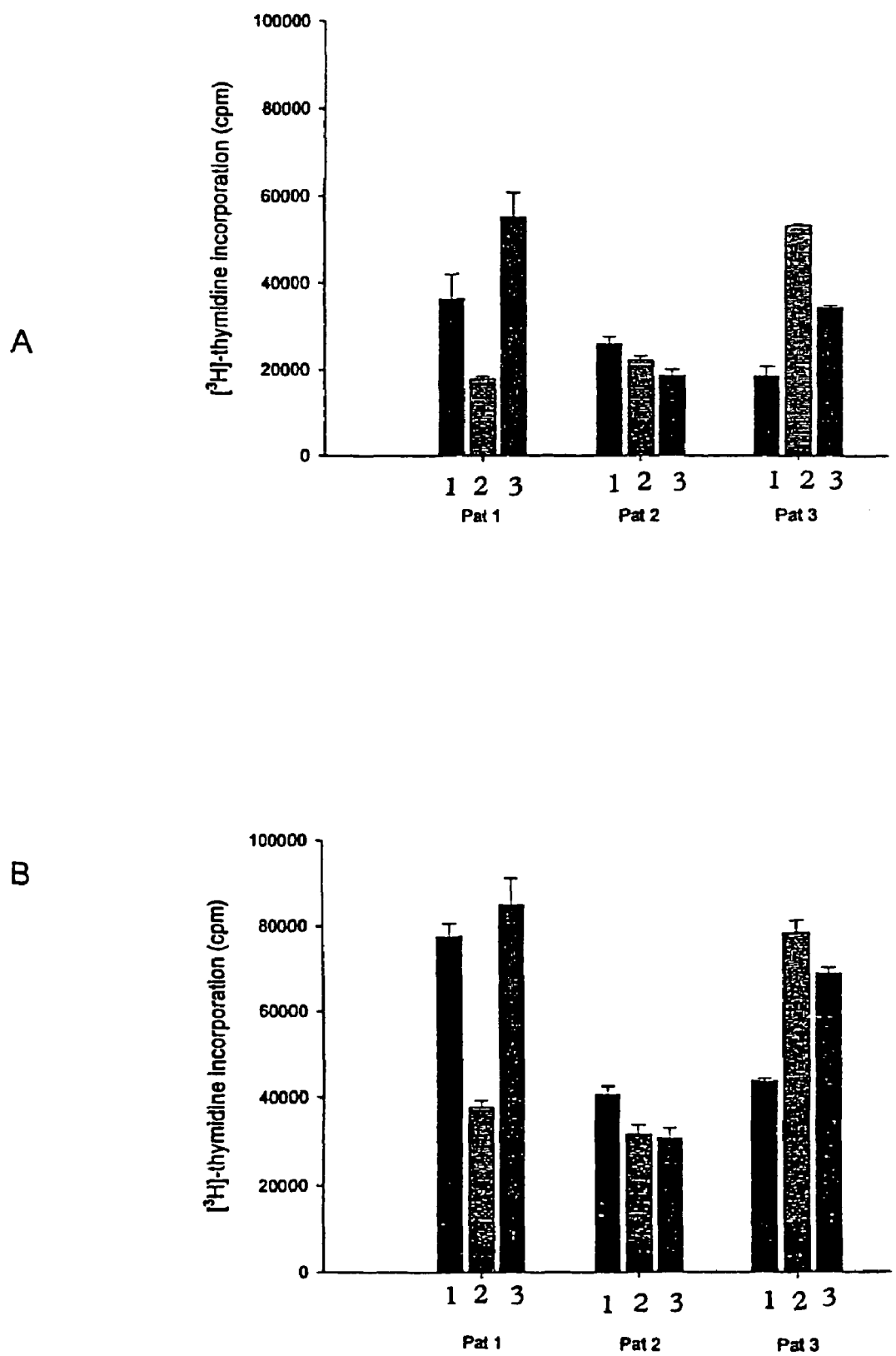
Figure 12:
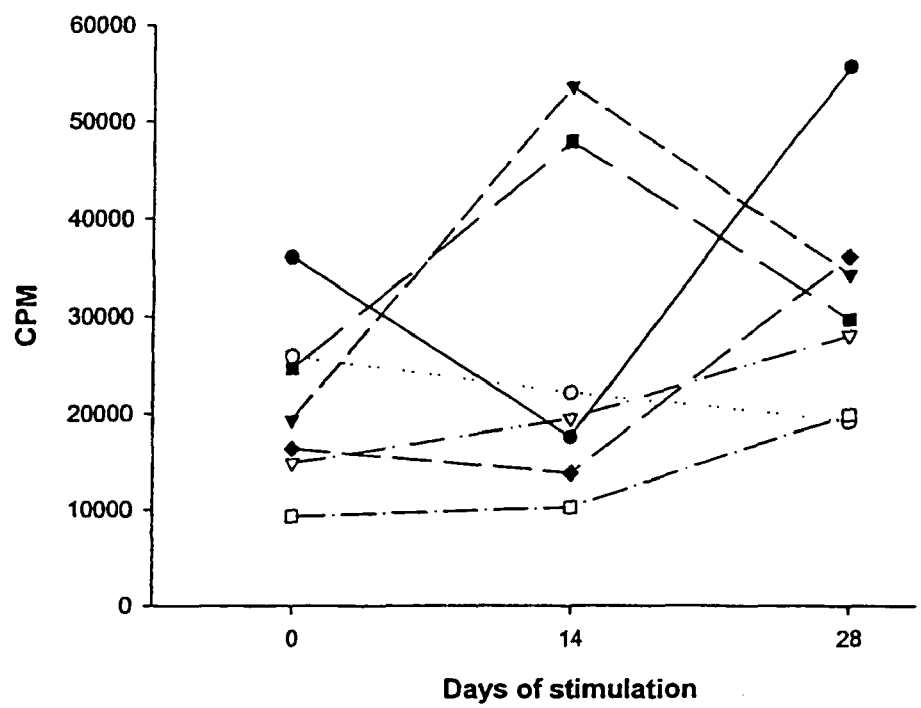
Figure 13:
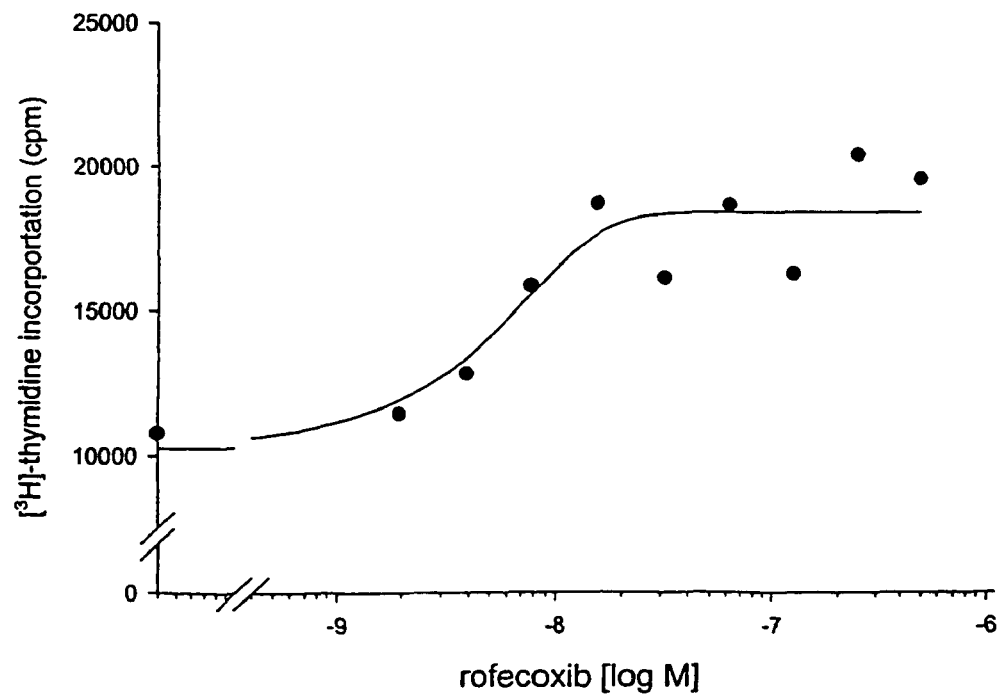
Figure 14:
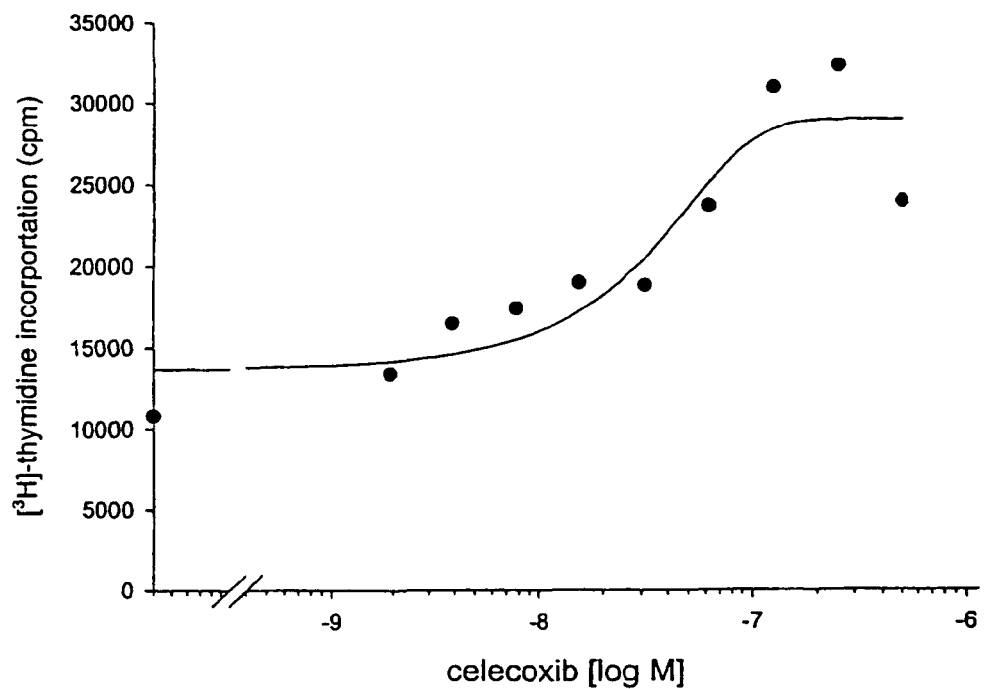
Figure 15:
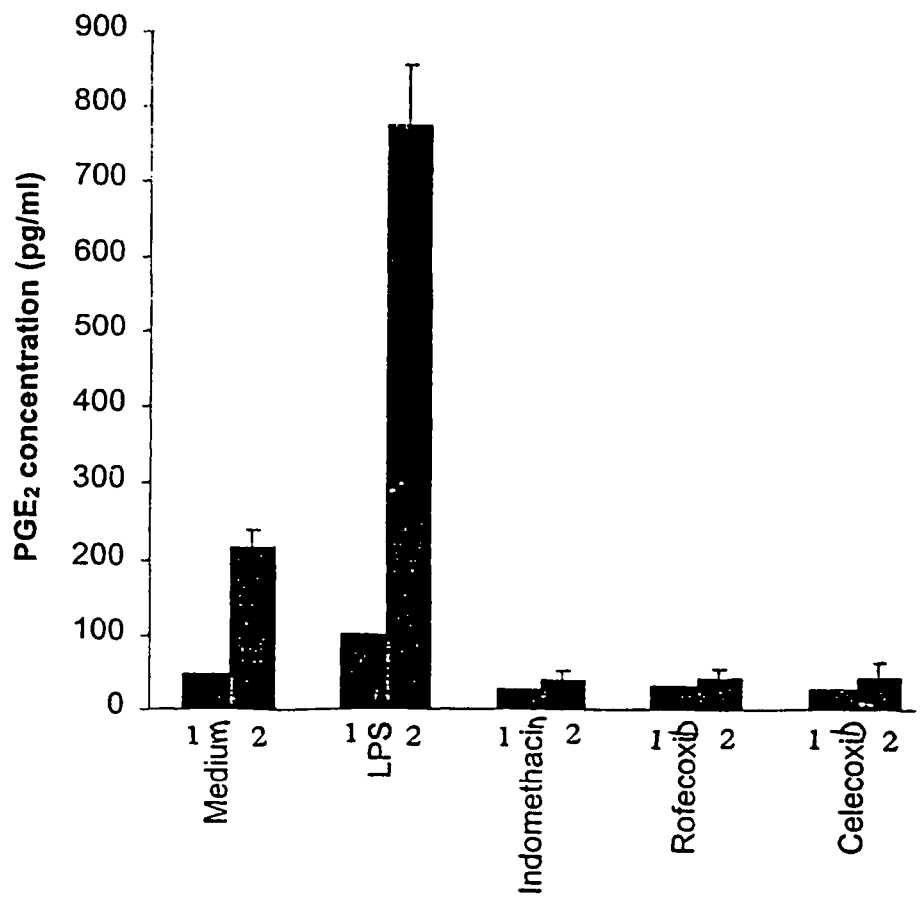
Figure 16:
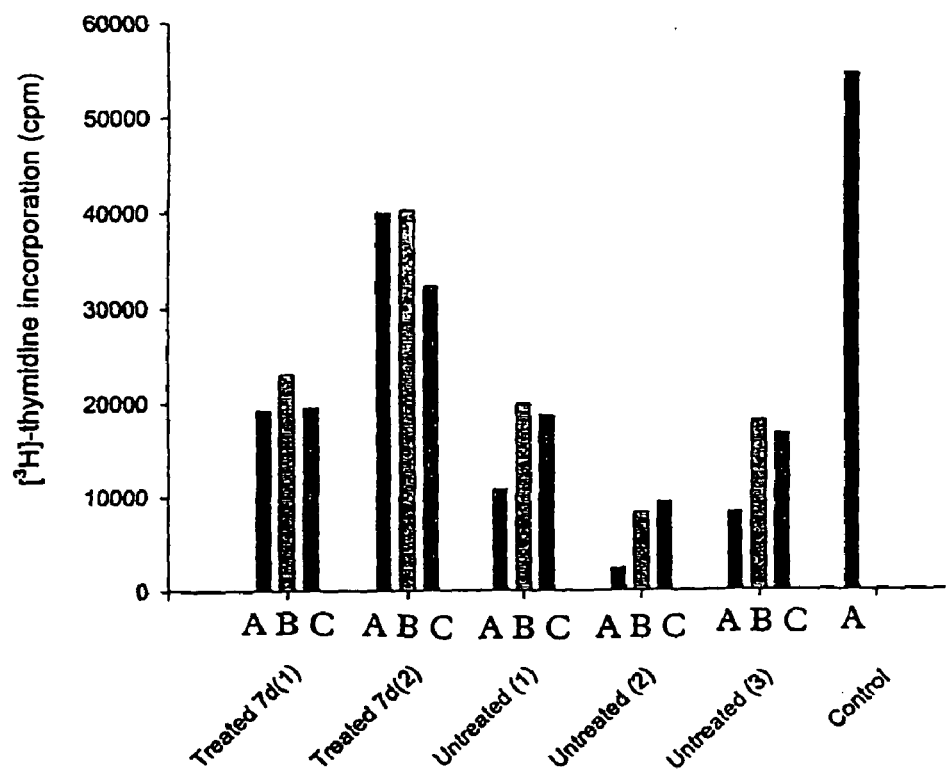
Figure 17:
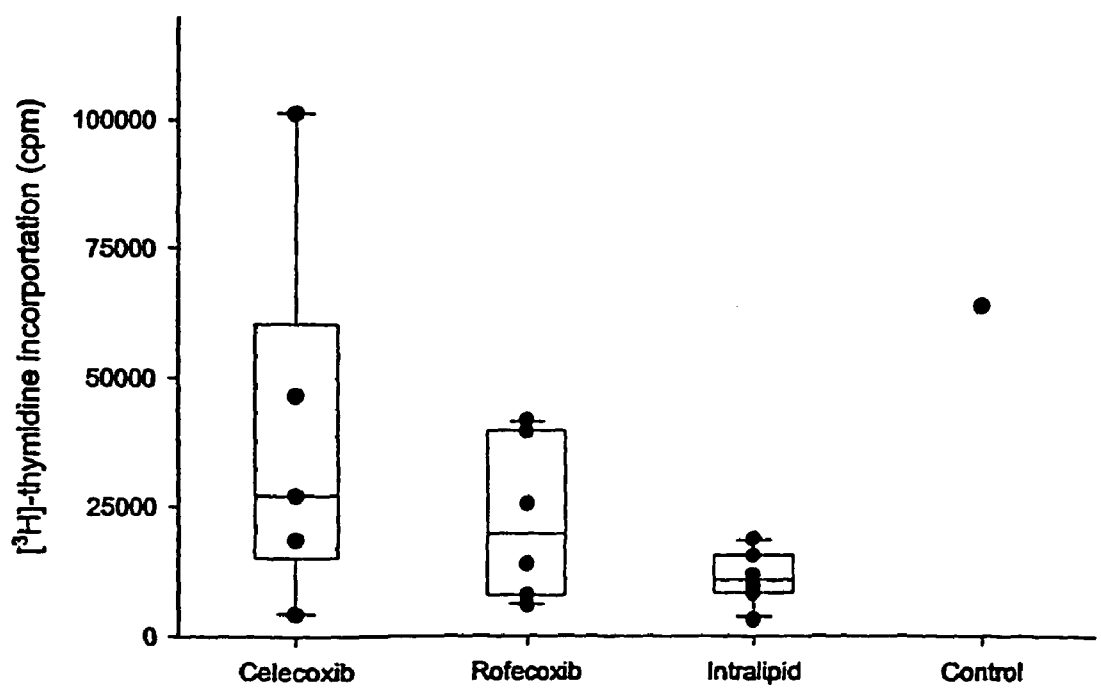
Figure 18:
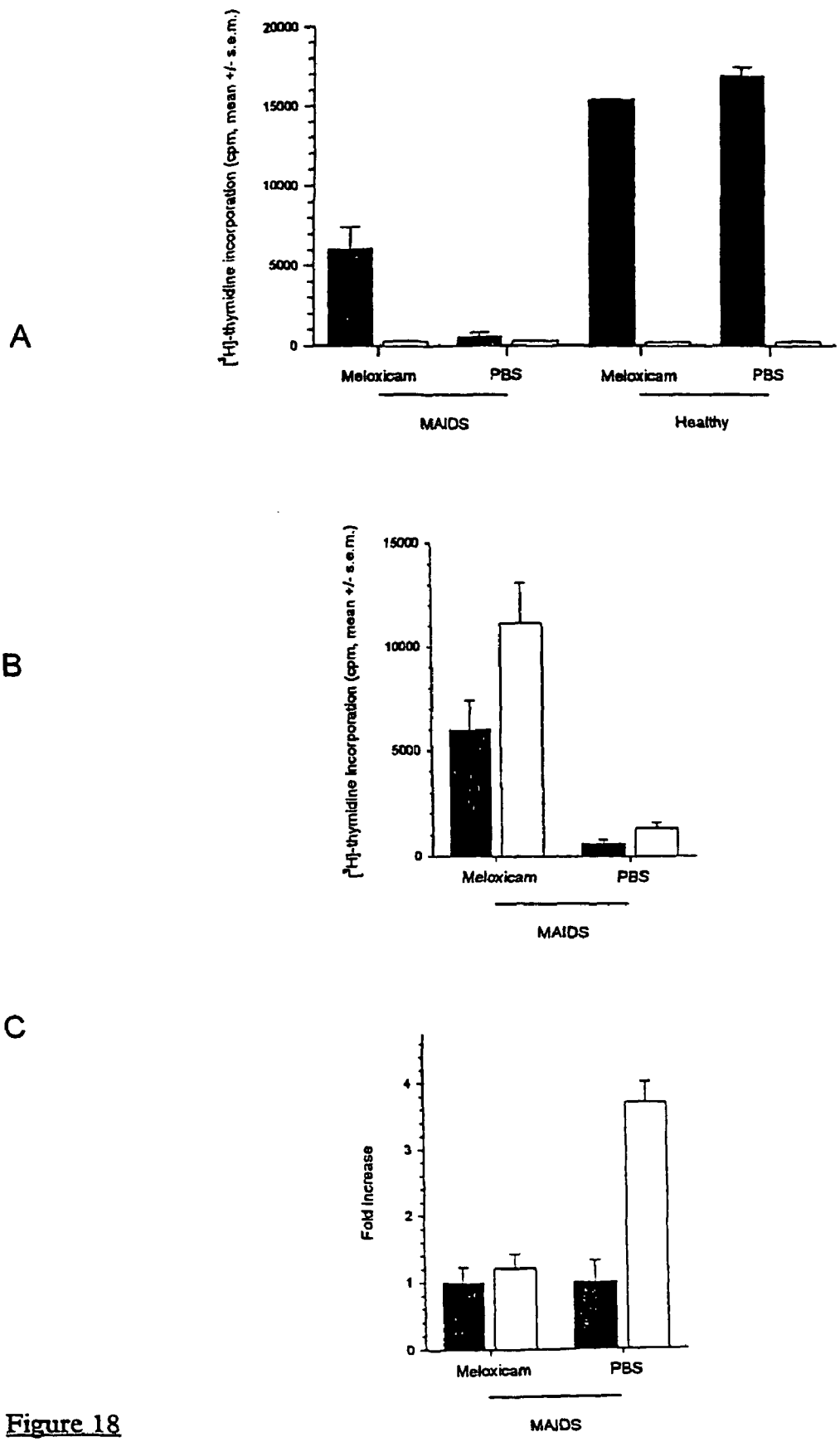

The invention is further described in the following non-limiting Examples with reference to the following Figures:

FIG. 1 shows cyclic AMP levels following MAIDS infection in CD8+ (A), CD4+ (B) and B (C) cells. Mononuclear cells were isolated from lymph nodes of mice infected with MAIDS for various periods of time and separated into CD4+, CD8+ and B cells by negative selection using a FACS-cell sorter. Intracellular cAMP levels were assessed by sonication and radioimmunoassay. Bars represent mean±SD (n=3 individual mice);

FIG. 2 shows MAIDS cAMP levels in CD4+, Thy-1.2 negative and positive populations. Lymph node cells from three infected and three age-matched control mice were FACS-sorted into CD4+, Thy-1.2+ (open bars) and CD4+, Thy-1.2− (solid bars) populations, and intracellular cAMP levels were assessed as in FIG. 1. Bars represent mean±SD (n=3);

FIG. 3 shows levels of protein kinase A activity in MAIDS vs wild type mice. (A) Kinase activities using Kemptide as substrate in the presence (total activity, hatched bars) or absence (free activity, solid bars) of 5 μM cAMP was examined in detergent-solubilized extracts of lymph node cells purified from mouse spleens. Phosphotransferase activity not inhibited by the PKA-specific protein kinase inhibitor (PKI, 1 μM) was subtracted to show only the PKA-specific activity. Activities in infected mice (MAIDS; n=4) are shown relative to those of wild type littermates. (B) [$^3$H-cAMP] binding was measured in the same extracts as in (A), and molar amounts of R monomer were calculated;

FIG. 4 shows immunolocalization of PKA C-subunit in cells of MAIDS and wild type mice. Mononuclear cells from control mice (upper panel) and mice infected with MAIDS (two lower panels) were attached to glass slides by cytospin (400×g), fixed and immunostained with anti-PKA-C polyclonal antibody and HRP-conjugated secondary antibody (brown stain). Counterstaining is by hematoxylin (blue stain on chromatin);

FIG. 5 shows the effect of the PKA type I antagonist Rp-8-Bromo-cAMP-phosphorothioate (Rp-8-Br-cAMPS) on T cell function in MAIDS and wild type mice. TCR/CD3 stimulated T cell proliferation was assessed with isolated T cells from MAIDS mice (A) and uninfected control mice (B). The effect of increasing concentrations of cAMP agonist (8-CPT-cAMP) on TCR/CD3 stimulated proliferation of CD3+ T cells isolated from MAIDS (open circles, dotted line) and control mice (filled circles and solid line) was examined separately in the same experiments (C). Mean values of triplicate determinations±SD are shown. See Table 4 for summarised data (n=11). Note: Scaling differs in A and B, whereas in C the TCR/CD3 induced proliferation in the absence of cAMP agonist is normalized to 100% for both MAIDS and control T cells;

FIG. 6 shows secretion of $PGE_2$ by normal and MAIDS lymph node cells in vitro. Unsorted lymph node cells from MAIDS infected mice (solid bars, n=9) at 20 weeks post infection and age-matched control mice (shaded bars, n=4) were cultured for 48 h in complete medium after which secreted levels of $PGE_2$ were measured in the supernatants by ELISA;

FIG. 7 shows the effect of a non-selective COX inhibitor on T cell immune function in normal and MAIDS infected mice. Column 1—control mice+anti-CD3; column 2—control mice+anti-CD3+indomethacin; column 3—MAIDS mice+ anti-CD3; column 4—MAIDS mice+anti-CD3+indomethacin. T cell proliferative responses were assessed in a mixed population of unsorted lymph node mononuclear cell by [$^3$H]-thymidine incorporation in the absence and presence of the non-selective COX inhibitor indomethacin (50 ng/ml). T cell activation was accomplished by cross-ligation of anti-CD3 (mAb 2C11; 4 μg/ml). Bars show mean values±SD from control (n=3) and MAIDS infected (n=5) mice, see Table 5 for additional data. Cells were cultured for 72 h during which [$^3$H] -thymidine was included for the last 4 h;

FIG. 8 shows expression of COX-2 by different subsets of lymph node lymphocytes in normal (A) and MAIDS infected (B) mice. CD4+ T, CD8+ T and B cells were FACS-sorted by positive selection on basis of expression of the CD4, CD8 and B220 molecules, respectively. CD11b—cells were sorted by negative selection (on the basis of absence of CD11b). Cells from MAIDS infected and normal mice were then lysed and 10 μg of protein from each sample were subjected to immunoblot analysis for the expression of COX-2. Blots were concomitantly reacted with antibodies to actin as control;

FIG. 9 shows expression of CD11b in MAIDS and wild type lymph node cells. Expression of CD11b (by flow cytometry) by the different subsets of lymph node lymphocytes (CD4+, CD8+ T cells and B220+ B cells) from MAIDS infected and control mice is shown. R1: CD11b high; R2: CD11b dim and R3: CD11b-.;

FIG. 10 shows levels of expression of COX-2 in lymph nodes of MAIDS infected mice and wild type mice. Lymph nodes were freeze-sectioned and subjected to COX-2 immunohistochemical staining (brown stain). (a) Normal control lymph node with germinal center stained for COX-2. (b) Normal lymph node at higher magnification. Cells staining positive for HRP-colour reaction are "tingible body" macrophages with ingested material (arrows). c. Lymph node from MAIDS infected mouse (week 20 post infection). Note: altered morphology and architecture. d. Higher magnification of MAIDS lymph node stained for COX-2. Note: number of cells brown immunostaining in the cytoplasm and numerous mitotic figures;

FIG. 11 shows the effect of in vivo administration of a non-selective COX inhibitor on T cell immune function of HIV infected patients. T cell proliferative responses were assessed in CD3+ T cells as [$^3$H]-thymidine incorporation from 3 patients (pat. 1 to 3) participating in a phase II clinical trial and receiving indomethacin 25 mg three times a day perorally for 14 days in addition to triple combination therapy. Upper panels shows T cell immune function at day 0, day 14 (after 2 weeks treatment) and at day 28 (2 weeks after discontinuation), labelled respectively as columns 1, 2 and 3. T cell activation was accomplished by cross-ligation of anti-CD3 (mAb SpVT3b). A: Basal proliferation after T cell activation; B: proliferation in presence of Rp-8-Br-cAMPS (1 mM); Note: degree of cAMP-mediated immunodeficiency is evident from comparing upper and lower panel. Bars show mean values±SD from triplicate determinations. Cells were cultured for 72 h during which [$^3$H]-thymidine was included for the last 16 h;

FIG. 12 shows the effect of in vivo administration of a non-selective COX inhibitor indomethacin on T cell proliferation of HIV infected patients as described in FIG. 11 but for 7 patients, indicated for patients 1 to 7, respectively by filled circles, open circles, filled triangles, open triangles, filled squares, open square and filled diamonds. Mean values from triplicate determinations are plotted, connector lines show development of each patient;

FIG. 13 shows the effect of rofecoxib, a COX-2 specific inhibitor, on T cell immune function in MAIDS infected mice. T cell proliferative responses were assessed in a mixed population of unsorted lymph node mononuclear cells by [$^3$H]-thymidine incorporation in the absence and presence of increasing concentrations (1.9 to 500 nM) of the COX-2 specific inhibitor, rofecoxib. T cell activation was accomplished by cross-ligation of anti-CD3 (mAb 2C11; 4 μg/ml). Mean values from triplicate determinations are shown together with a sigmoid curve fit. Cells were cultured for 72 h during which [$^3$H ]-thymidine was included for the last 4 h;

FIG. 14 shows the effect of celecoxib, a COX-2 specific inhibitor, on T cell immune function in MAIDS infected mice, as described in FIG. 13 for rofecoxib;

FIG. 15 shows the effect of rofecoxib and celecoxib compared to indomethacin on the secretion of $PGE_2$ by lymph node (LN) cells ex vivo for control mice (1) or MAIDS mice (2). Unsorted LN cells were cultivated in complete medium in the presence or absence of the $PGE_2$ inducer, lipopolysaccharide (LPS; 4 µg/ml); the nonspecific cyclooxygenase inhibitor, indomethacin (50 ng/ml); and the COX-2 specific inhibitors rofecoxib (0.125 µM) and celecoxib (0.125 µM). After 48 h, the concentration of $PGE_2$ was measured by EIA in the supernatants. 3 individual infected mice (week 20) and pool of 3 age-matched controls were analyzed. Means±standards deviations are shown; and FIG. 16 shows the effect of in vivo treatment of MAIDS mice with rofecoxib on T cell immune function. MAIDS mice were left untreated (untreated 1 to 3) or treated with rofecoxib per os (3 mg/kg/day administered once daily, treated 1 and 2) for seven days administered via a tube inserted in the ventricle. Subsequently, T cell proliferative responses were assessed in vitro in a mixed population of unsorted lymph node mononuclear cells from treated and untreated animals by [$^3$H]-thymidine incorporation in the absence (columns A) and presence of Rp-8-Br-cAMPS (0.5 or 1.0 mM, columns B and C, respectively). T cell activation was accomplished in all samples by cross-ligation of anti-CD3 (mAb 2C11; 4 µg/ml). Control represents T cell proliferation in uninfected mice. Mean values from triplicate determinations are shown. Cells were cultured for 72 h during which [$^3$H]-thymidine was included for the last 4 hours;

FIG. 17 shows the effect of in vivo treatment of MAIDS mice with rofecoxib or celecoxib on T cell immune function. MAIDS mice were injected with vehicle (intralipid), treated with rofecoxib in intralipid by intraperitoneal injection (3 mg/kg/day administered once daily, n=6) or treated with celecoxib by intraperitoneal injection (20 mg/kg/day administered once daily, n=5) for 18 to 20 days. Subsequently, T cell proliferative responses were assessed in vitro as described for FIG. 16 but without Rp-Br-cAMPs. Control represents T cell proliferation in uninfected mice. Mean values from triplicate determinations are shown (black circles) along with 25 to 75% percentile (boxed areas) and median (line in box). Bars represent range; and FIG. 18 shows the effect of in vivo treatment of MAIDS mice with meloxicam on T cell immune function. Osmotic pumps (Alzet, 100 µl) with meloxicam (release rate of 70 µg/animal/day) or phosphate buffered saline (PBS) were implanted subcutaneously on MAIDS mice (14 weeks post infection) and healthy mice for 14 days. a), Subsequently, T cell proliferative responses were assessed in vitro as described for FIG. 17. Mean values±standard error of the mean (s.e.m.) from each group are shown. The effect of meloxicam treatment on anti-CD3 stimulated proliferation of cells from MAIDS mice (solid bars) compared to that of MAIDS mice that received PBS (open bars) is significant ($p<0.05$). b), Mixed lymph node cultures from the groups of mice in a) treated in viva with meloxicam or PBS were added back meloxicam (2.5 µg/ml) in cell culture in vitro, anti-CD3 induced T cell proliferation was assessed as in a), and the effect of meloxicam added back in vitro (open bars) was compared to the response of the cells with no in vitro addition (solid bars) ($p=0.005$). c), Rp-8-Br-cAMPS (0.5 mM) was added to in vitro cell cultures of mixed lymph node cultures from the groups of mice in a) treated in vivo with meloxicam or PBS, anti-CD3 induced T cell proliferation was assessed as in a), and the effect of Rp-8-Br-cAMPS in vitro (open bars) was expressed as fold induction above that of cells that received no in vitro addition (solid bars). Statistics were analysed by Mann-Whitney U test for comparison of two groups of animals and with Wilcoxon Matched Pairs Test for comparison of the same group with two different treatments.

EXAMPLES

Example 1

Mice with Murine Acquired Immunodeficiency Syndrome (MAIDS) have a cAMP/PKA Type I Induced T Cell Dysfunction MAIDS (Murine Acquired Immunodeficiency Syndrome). Numerous studies have considered MAIDS as a possible model for infection of humans by HIV. This syndrome develops following infection with a replication-defective retrovirus that encodes a variant Pr60$^{gag}$ polyprotein (Chattopadhyay et al., 1991, J. Virol., 65, p4232-4241; Jolicoeur, 1991, FASEB J., 5, p2398-2405). The syndrome is associated with progressive lymphoproliferation in the spleen and lymph nodes and severe immune defects. Although the defective retrovirus responsible for MAIDS infects mostly B cells (Aziz, 1989, Nature, 338, p505-508), CD4$^+$ T cells display a profound dysfunction and anergy to mitogen stimulation in vitro. A large fraction of CD4$^+$ T cells (but not CD8$^+$ T cells) of infected mice are also characterized by an unusual Thy-1 negative phenotype (Holmes et al., 1990, Eur. J. Immunol., 20, p2783-2787; Moutschen et al., 1994, Scand. J. Immunol., 39, p216-224 (MAIDS)). In normal, uninfected mice, CD4$^+$ Thy-1$^-$ T cells are found selectively in the germinal centers where they correspond to recent antigen-specific emigrants.

The mechanism by which the variant Pr60$^{gag}$ protein induces T cell abnormalities is not known. Soluble factors secreted by infected cells have been claimed to influence the function of T cells (Simard, J. Virol., 68, p1903-1912) at a distance, but the nature of such mediators has never been elucidated. Other studies have suggested that direct, cognate interactions between CD4$^+$ T cells and antigen presenting cells are necessary for the induction of T cell defects (Green, 2001, J. Virol., 70, p2569-2575; de Leval, 1998, J. Virol., 72, p5285-5290.

The adenylate cyclase-cAMP-protein kinase A pathway plays an important role in the regulation of immune responses (Kammer, 1991, Immunol. Today, 9, p222-229). Increased concentration of cAMP is known to inhibit proliferative responses of T cells to various stimuli such as anti-CD3 mAb and interleukin-2. A recent report has suggested that down-regulation of the JAK3 tyrosine kinase might represent a mechanism by which cAMP inhibits T cell proliferation (Kolenko, 1999, Blood, 93, p2308-2318). Cyclic AMP could also induce the downregulation of membrane proteins since murine thymocytes or thymoma cells exposed to cAMP inducing agents such as norepinephrine downregulate Thy-1 expression by a mechanism involving destabilization of mRNA (Wajeman-Chao, J. Immunol., 161, p4825-4833).

Prostaglandin $E_2$ ($PGE_2$), a potent inducer of cAMP, is mainly secreted by monocytes, macrophages and activated T cells. $PGE_2$ shifts the balance from T-helper type 1 cells toward T-helper type 2 cells by inhibiting IL-2 and enhancing IL-4 production (Betz and Fox, 1991, J. Immunol., 146, p108-113; Meyaard, 1997, Blood, 89, p570-576). It also skews the differentiation of B cells toward IgE production (Fedyk and Phipps, 1996, PNAS USA, 93, p10978-10983). Prostaglandin synthesis results from the sequential action of cyclooxygenase-1 and -2 (COX-1 and COX-2) and specific PG synthases (Smith and DeWitt, 1996, Adv. Immunol., 62, p167-215). While COX-1 expression is largely constitutive and ubiquitous, COX-2 is only induced in certain cell types (macrophages, fibroblasts, smooth muscle cells) by NO and inflammatory cytokines such as IL-1 and TNF-α.

The mechanisms responsible for T cell dysfunction in MAIDS are still poorly understood. $CD4^+$ T cells are preferentially involved whereas several reports have suggested that the alteration of $CD8^+$ T cells is only due to the lack of adequate $CD4^+$ T cell help. In contrast, the inhibition of B cell responses is intrinsic and cannot solely be explained by defective $CD4^+$ lymphocytes. The Inventors' observation of a selective increase of cAMP in B cells and $CD4^+$ T cells and not in $CD8^+$ T cells is therefore compatible with the involvement of cAMP in the anergic process associated with MAIDS.

To the Inventors' knowledge, this is the first demonstration of a subset selective increase of cAMP in a disease model. If a soluble factor such as prostaglandin $E_2$ is indeed responsible for cAMP induction, what could explain the subset selectivity of its action? Former studies had compared the expression of various prostanoid receptors on $CD4^+$ and $CD8^+$ T cells and concluded a similar pattern of expression in both subsets. Normal $CD8^+$ T cells are fully susceptible to the cAMP inducing effects of $PGE_2$. A possible explanation could take place at the post receptor level; memory/activated T cells are more responsive to $PGE_2$ than naive T cells. In MAIDS, where MHC class II-dependent processes are involved, $CD4^+$ T cells could acquire a particular state of activation making them more susceptible to the effect of a given concentration of $PGE_2$. Postreceptor modulation of prostanoid effects is principally mediated by G receptor kinases (GRK) which uncouple protein G from the corresponding membrane receptor. Inflammatory states such as rheumatoid arthritis are characterised by a downregulation of GRK and therefore by an increased lymphocyte sensitivity to cAMP inducing agents such as catecholamines. Levels of GRK activity in $CD4^+$ and $CD8^+$ T cells from infected mice is unknown.

Methods Used in Examples 1 and 2

Mice and Cell Suspension

Male C57BL/6 mice were bred in the Inventors' facility. Mice were injected twice i.p at the age of 4 and 5 weeks with 0.25 ml of the cell free viral extract. Age-matched control mice were injected twice i.p. with 0.25 ml phosphate buffered saline (PBS). At different times post-infection, mice were killed by $CO_2$ asphyxiation. Peripheral lymph nodes (inguinal, axillary and cervical) were dissociated with syringes to obtain single cell suspensions and passed through a nylon cell stainer, washed three times with RPMI 1640 complete medium and counted on Thoma cytometer after trypan blue exclusion.

Virus

Viral extract was prepared from lymph nodes of mice injected 2 months earlier with RadLV-Rs as described previously. Lymph nodes were collected, ground in PBS and centrifuged at $1.5\times10^4$ g for 30 min. The supernatant was spun again for 30 min at $1.5\times10^4$ g. This acellular viral extract was stored in liquid nitrogen. XC plaque assay was used to quantify the viral particles. The viral preparation contained $10^3$ particle forming units (PFU) ecotropic virus/ml.

Antibodies

The following polyclonal antibodies were used for western blotting experiments; Primary: polyclonal rabbit anti-COX-1 or rabbit anti-COX-2 antibody. (Santa Cruz Biotechnology); Second-step: Horseradish Peroxidase Conjugated anti-rabbit was purchased from Transduction Laboratories (Transduction Laboratories, UK). For the flow cytometry, the moAbs used are as follows: PE-conjugated CD4/L3T4 (YTS.191.1), FITC-conjugated CD45R/B220 (RA3-6B2), FITC-conjugated CD11b/Mac-1 (M1/70), FITC-conjugated CD161/NK-1.1 (PK136), FITC-conjugated CD8a (Ly-2) and CD16/CD32 (FcγIII/II Receptor) (2.4G2), (all from Pharmingen: San Diego, Calif., USA). CD3 moAb (145-2C11) was purified in the Inventors' laboratory. Concanavalin A (ConA) was purchased from Boehringer Mannheim Biochemica and phytohemagglutinin-M (PRA) from Difco.

Flow Cytometry and Cell Sorting

Analysis were performed by using FACStar-plus flow cell sorter with the Cellquest software (Becton Dickinson). The forward and side scatters were used to gate viable lymphocytes. For two-colour analysis of FITC (green) and PE (orange), blue excitation at 488 nm was provided by an argon ion laser (Air-to-Water cooled model Spinnaker 1161; Spectra Physics, Mountain View, Calif.) For cell sorting, $60\times10^6$ cells were incubated with anti-FcγRII (Fc Block) to prevent non specific interactions, prior to labelling for 20 min on ice with the fluorochrome-conjugated antibodies. $CD4^+$ T cells were negatively selected by depleting $CD8^+$ $B220^+$ $CD11b^+$ cells. Similarly, $CD8^+$ T cells were negatively selected by depleting $CD4^+$ $B220^+$ $CD11b^+$ cells and B cells by depleting $CD8^+$ $CD4^+$ $CD11b^+$ cells. For each sorting, the selected fraction was reanalyzed by flow cytometry to assess purity which was always higher than 97%.

Cyclic AMP Quantitation

Single lymph node cell suspensions were prepared as described above, washed twice with RPMI 1640 and centrifuged at 1500×g for 3 min. Cells were subsequently disrupted by sonication to facilitate the release of intracellular cAMP into the extraction solution (0.01N HCl, 95% ethanol). The solution containing the cell lysate was centrifuged at $13\times10^4$×g for 15 min, and the supernatant was removed to a fresh tube. The extract was evaporated in a Speed Vac concentrator at 45° C., and the pellet was stored at −20° C. Just before use, the pellet was resuspended in the assay buffer and cAMP levels were measured by radioimmunoassay (RIA) using $^{125}$I-Labelled cAMP assay system (Amersham, England). The concentration of cAMP in test samples was determined by comparison with a curvi-linear standard curve. For positive and negative controls, lymph node cells ($1\times10^6$) were incubated respectively with 1 mM of dDibutyryl-cAMP and 0.5 mM of DDA (Adenylyl cyclase inhibitor) for 30 min at 37° C. in a humidified 5% $CO_2$ air incubator before measurement of cAMP concentration.

Cell Homogenization and Immunoblotting

Cells ($50\times10^6$) were homogenized by sonication (2×15 s) on ice in a buffer containing 10 mM potassium phosphate, pH 7.1, 250 mM sucrose, 1 mM EDTA, 0.1% triton X-100 and 10 μg/ml each of the protease inhibitors chymostatin, leupeptin, pepstatin A and antipain (Tasken et al, 1993, J. Biol. Chem., 268, p21276-21283), and centrifuged for 30 min (15,000×g) to remove unsoluble material. Protein concentrations were determined by Bradford assays (BioRad). For immunoblotting, 40 μg of protein was separated by 10% SDS-PAGE, transferred to PVDF membranes and incubated with antibodies in TBS/Tween with 5% non-fat dry milk and 0.1% BSA (Blotto). Primary antibodies were detected by HRP-conjugated secondary antibodies (Jackson Laboratories/Transduction Laboratories) and ECL (Amersham).

Phosphotransferase Activity of PRA

Catalytic activity of PKA was assayed by phosphorylating a PKA-specific substrate (Leu-Arg-Arg-Ala-Ser-Leu-Gly)

(Kemp et al, 1976, PNAS USA, 73, p1038-1042) Kemptide, Peninsula Laboratories INC.) using [γ-$^{32}$P]-ATP (specific activity 0.25 Ci/mMol, Amersham) in an assay mixture described by R. Roskoski (Methods Enzymol., 1983, 99, p36). Phosphotransferase activity was measured both in the presence and absence of cAMP (5 μM) and PKI (1 μM), and the low levels of activity not inhibited by PKI was subtracted to determine PKA-specific activity.

Cyclic AMP Binding Measurements

Quantification of specific [$^3$H]cAMP binding of solubilized PKA regulatory subunits was performed as described by Cobb and Corbin (Methods in Enzymology, 159, p202-208, 1988) in a mixture containing [2,8-3H]CAMP (2.25 μM; specific activity of 5 Ci/mMol; Du Pont-New England Nuclear). Molar ratios of R subunits were calculated based on two cAMP binding sites on each regulatory subunit monomer.

Immunocytochemistry

Control and infected lymph node lymphocytes were fixed with cold acetone for 5 min and washed twice for 5 min each in 0.1% of saponin in PBS. Endogenous peroxidase was blocked by incubation with 0.3% hydrogen peroxide in 0.1% saponin/PBS for 15 min. After rinsing in saponin/PBS, the slides were incubated for 30 min at RT with blocking buffer (1.5% normal goat serum in 0.1% saponin/PBS), followed by incubation for 60 min with primary antibody solution at RT in a humidified chamber. Antibody against Cα was from Santa Cruz and was diluted at 1:1000 in PBS containing 0.1% of saponin and 0.5% of normal goat serum. Slides were then washed as before and incubated with biotinylated goat anti-rabbit antibody. This later was detected by ABC complex (Novastain Super ABC Kit, Novocastra). Peroxidase was revealed using diaminobenzidine (DAB) (Dako) which gives a brown precipitate in the presence of $H_2O_2$. Slides were counterstained with hematoxylin-eosin (Sigma). The specificity was tested by incubating the cytospin with specific peptide against the PKA-Cα subunit.

Immunohistochemistry

Immunohistochemistry was performed on 2 μm-thin histological sections done in 4% paraformaldehyde fixed and plastic embedded tissues (JB4-JBPolysciences). Sections were permeabilized with trypsin (0.24%) for 1 min at 37° C., and then with Tween 20 (2%) for 30 min at 37° C. Endogenous peroxidases were quenched by incubation with $H_2O_2$ (1%) for 30 min at room temperature. Aspecific sites were saturated with normal goat serum (1.5%) during 1 h at 37° C. Sections were then incubated overnight at 4° C. with primary polyclonal rabbit anti-COX-1 or rabbit anti-COX-2 antibody (Santa Cruz Biotechnology) and then for 2 h with biotinylated goat anti-rabbit antibody. This later was detected by ABC complex (Novostain Super ABC Kit, Novocastra). Peroxidase was revealed using diaminobenzidine (DAB) (Dako) which gives a brown precipitate in the presence of $H_2O_2$. Sections were counterstained with haematoxylin-eosin (Sigma). The specificity was tested by incubating sections with normal rabbit serum instead of primary antibody.

Proliferation Assays for MAIDS Mice

Proliferation assays were performed by incubation of 0.1× 10$^6$ CD3+ T cells/ml in a 100 μl volume in flat-bottom 96-well microtiter plates. Activation was achieved by subsequent addition of monodisperse magnetic beads coated with sheep anti-mouse IgG (Dynal, cat. no. 110.02) at a cell:bead ratio of 1:1 followed by addition of anti-CD3 (clone 2C11) at a final dilution of 4 μg/ml for the experiments shown. The optimal concentration of antibody was titrated carefully in the initial setup and parallel experiments at several different dilutions of antibody was always performed. Proliferation was analyzed by incubating cells for 72 hours during which [$^3$H]-thymidine (0.4 μCi) was included for the last 4 hours and collected into a cell harvester (Skatron, Sterling, Va., USA) onto glass fiber filters. Incorporated precursor was counted in a scintillation analyzer (Tri-Carb, Packard, Meriden, Conn., USA). cAMP analogs, when used, were added 30 min prior to activation by addition of anti-CD3 antibodies. 8-CPT-cAMP was from Sigma (St. Louis, Mo.) and Sp- and Rp-8-Br-cAMPS were from BioLog Life Science Company (Bremen, Germany) and were all dissolved to concentrations of 4 to 10 mM in PBS and concentrations calculated using the extinction coefficients given by the manufacturer. Indomethacin was dissolved in water and used at a concentration of 50 ng/ml.

$PGE_2$ Determination

500 μl of a 48 h-culture supernatant of lymph node cells from control and infected mice were pipetted into 1.5 ml polypropylene tubes to which were added 500 μl of water: ethanol (1.4) and 10 μl of ice cold acetic acid. The tubes were gently mixed and left for 5 min at room temperature. This was followed by centrifugation at 2500×g for 2 min. The supernatants were collected and run through Amprep C18 minicolumns, which had been primed with 2 column volumes of 10% ethanol. The columns were then washed with 1 volume of $H_2O$ and 1 column volume of hexane. $PGE_2$ was then eluted with 2×0.75 ml of ethyl acetate. The fractions were collected and evaporated under nitrogen to dryness. Finally, each fraction was reconstituted in 100 μl of assay buffer and $PGE_2$ was assayed using Amersham EIA kit as recommended by the manufacturer.

Statistical Analyses

For comparison of two groups of individuals, the Mann-Whitney U test (two-tailed) was used. Coefficients of correlation (r) were calculated by the Spearman=s rank test. Statistical and curve fit analyses were performed using Statistica (Statsoft Inc., Tulsa, Okla.) and Sigma Plot (Jandel Corporation, Erkrath, Germany) software packages, respectively. Results are given as medians and 25th to 75th percentiles if not otherwise stated, p-values are two-sided and considered significant when <0.05.

Experimental

MAIDS infection leads to elevated CAMP in CD4+ T cells—Mice inoculated with a mixture of retroviruses known as RadLV-Rs that causes development of MAIDS, were sacrificed at different time points after infection, and lymph node cells were sorted by negative selection using a flow cytometer/cell sorter into pure B cells and CD4+ and CD8+ T cells. Intracellular cAMP levels were assessed in the different cell populations following infection. As can be seen from FIG. 1, cAMP levels were strongly increased (more than 20-fold) in CD4+ T cells after a few weeks of infection. At later stages, B-cell cAMP levels also increased whereas only minor changes were observed in CD8+ T cells. Furthermore, when CD4+ T cells were separated into Thy-1.2+ and Thy-1.2− cells by positive sorting, it was evident that the major increase in CAMP levels was in Thy-1.2− cells (FIG. 2, 6-fold). This normally low-abundant population also displayed higher basal levels of cAMP than compared to those of the Thy-1.2+ when both populations were harvested from uninfected mice.

Examination of PKA phosphotransferase activity in postnuclear supernatants from detergent solubilized extracts revealed that the total levels of cAMP-dependent kinase activity was decreased in MAIDS lymph node cells whereas minor changes in the activity were observed in the absence of cAMP (FIG. 3A). This is consistent with a chronic activation and dissociation of PKA leading either to degradation of the C subunit or to translocation of C. Assessment of CAMP binding (FIG. 3B) revealed no changes in total levels of PKA R subunits. Immunocytochemistry of lymph node cells from MAIDS—and control mice revealed increased levels of immunoreactive PKA C subunit in the nucleus (FIG. 4). This is again consistent with an activation of the cAMP-PKA pathway in MAIDS.

PKA Type I Antagonist Improves T Cell Proliferation of MAIDS T Cells—

In order to examine the effect of elevated cAMP and activation of PKA on inhibition of TCR/CD3-induced T cell proliferation, we used a sulfur-substituted cAMP analog (Rp-8-Br-cAMPS) working as a full antagonist for PKA type I (Gjertsen, Mellgren, et al. 1995 1665/id). FIG. 5A shows that in T cells from MAIDS-infected mice, TCR/CD3-stimulated proliferation was less than 10% of that of T cells from uninfected control mice (FIG. 5B). Furthermore, when the effect of the PKA type I antagonist was assessed in MAIDS T cells, we observed a concentration-dependent increase in TCR/CD3-induced proliferation that was more than 4-fold at higher concentrations (FIG. 5A), whereas no stimulation was observed by treatment of control T cells (FIG. 5B). Looking at eleven MAIDS-infected mice, they all had severely impaired T cell proliferation compared to controls ($p<0.001$) and in 10 out of 11 mice, the PKA type I antagonist improved T cell proliferation ($p<0.01$; median 2.2-fold, Table 5). The stimulatory effect of the cAMP antagonist was not saturated even at the highest concentrations used (FIG. 5A and similar data (not shown) were obtained for all mice in Table 5). This indicates that the solubility of the compound, affinity, or availability to cells may be a limiting factor for the effect observed. Thus, a more permeable and potent PKA type I antagonist, when available, may further improve TCR/CD3-induced proliferation of MAIDS T cells.

Next, the effect of cAMP agonist on TCR/CD3-induced proliferation was investigated in five MAIDS-infected mice and four controls. T cells from MAIDS-infected mice revealed an apparent shift in sensitivity to inhibition of cell proliferation by exogenously added 8-CPT-cAMP (FIG. 5C and Table 5). Moreover, when the maximal proliferation rates of T cells from MAIDS-infected mice and that of control T cells were normalized to 100% (FIG. 5C and data not shown), it was evident that in addition to a left-shifted cAMP-inhibition curve, the slopes of the curves were significantly different (Hill coefficients of 0.6 (0.54 to 1.52) for T cells from MAIDS mice versus 2.2 (1.9-2.5) for normal T cells, Table 5, $p<0.05$). The increased sensitivity to inhibition by cAMP analog suggests a contribution from elevated endogenous cAMP in priming cAMP binding site B of PKA type I with subsequent increase in the affinity of the A site for the exogenously added cAMP analog. The shift in curve slope from a cooperative, two-ligand site binding situation to an apparent non-cooperative inhibition curve by 8-CPT-cAMP also indicates B-site occupancy by elevated endogenous cAMP.

TABLE 5

| Mice | Anti-CD3-induced proliferation (cpm) | Increase in proliferation by Rp-8-Br-cAMPS (fold increase) | Inhibition of proliferation by 8-CPT-cAMP ($IC_{50}$, μM) | Inhibition of proliferation by 8-CPT-cAMP (Hill coefficient) |
|---|---|---|---|---|
| 1 | 9525 | 19 | 6 | .41 |
| 2 | 3312 | 24 | 22 | .54 |
| 3 | 9153 | 14 | 8 | .58 |
| 4 | 959 | 37 | n.d. | n.d. |
| 5 | 13791 | 10 | 52 | 1.56 |
| 6 | 6370 | 19 | 66 | 1.52 |
| 7 | 6357 | 22 | n.d. | n.d. |
| 8 | 9986 | 42 | n.d. | n.d. |
| 9 | 5696 | 40 | n.d. | n.d. |
| 10 | 16132 | 37 | n.d. | n.d. |
| 11 | 3740 | 37 | n.d. | n.d. |
| MAIDS Median (25-75th percentiles) | 6370* (3740-9986) n = 11 | 2.2** (1.9-3.7) n = 11 | 0.22 (0.08-0.52) n = 5 | 0.58*** (0.54-1.52) |
| Controls Median (25-75th percentiles) | 62281 (56539-82038) n = 6 | 1.1 (1.0-1.3) n = 6 | 0.40 (0.33-0.46) n = 4 | 2.24 (1.93-2.47) n = 4 |

MAIDS vs. controls; *denotes $p < 0.001$, denotes $p < 0.01$ and *denotes $p < 0.05$ Example 2

Cyclic AMP-induced T Cell Dysfunction of MAIDS is Due to Increased $PGE_2$ Production by CD11b-positive Cells with Increased Levels of COX-2

Elevated Production of $PGE_2$ in MAIDS—

Mixed lymph node cell populations were isolated from MAIDS-infected and control mice and cultured in vitro. Secreted levels of $PGE_2$ were assessed in media supernatants after 48 hours of culture and revealed that MAIDS infected cells secreted 7 to 8-fold more $PGE_2$ than control cells.

Inhibition of $PGE_2$ Production Restores the T Cell Proliferation in MAIDS—

Next, mixed lymph node cells were activated by anti-CD3 antibodies to induce proliferation of T cells, and [$^3$H]-thymidine incorporation was examined after 72 hours. Proliferation of cells from MAIDS-infected mice was again only 10 to 20% of the T cell proliferation of uninfected cells. However, when indomethacin was added to the cultures to inhibit production of $PGE_2$ in the mixed cultures, this strongly increased the proliferation of cells from five MAIDS-infected mice to levels comparable to that of control mice (FIG. 6). Looking at 10 additional MAIDS-infected mice (Table 6), the effect of indomethacin on T cell proliferation of mixed lymphocyte cultures was very significant (p<0.01). In contrast, treatment of control cultures with indomethacin did not alter proliferation.

COX-2 is Expressed at High Levels in Lymph Nodes of MAIDS Infected Mice—

The constitutively expressed COX-1 is the normal source of cyclooxygenase activity that produces $PGE_2$. However, no increase in COX-1 could be found in MAIDS mice that could account for the increased levels of $PGE_2$ (data not shown). Expression of COX-2 is normally restricted to brain/brain processes, to arthritic synovia and sites of tissue injury. COX-2 is not found in lymph nodes or lymphocytes as shown e.g. for control lymphocytes in FIG. 8 (upper panel). Surprisingly, we found that crude lymph node cells from MAIDS infected mice express high levels of COX-2 (FIG. 8, lower panel). Furthermore, positively selected CD4+ and CD8+ T cells as well as B cells from MAIDS lymph nodes contained high levels of COX-2. In contrast, negatively selected CD11b-cells contained only low levels of COX-2.

From looking at CD4+ and CD8+ T cells and B cells (B220 marker) from MAIDS infected and control mice by flow cytometry, it was evident that the CD11b marker is not normally expressed on T or B cells. However, a distinct fraction of both CD4+ T cells and B cells from MAIDS infected mice were CD11b bright (gating labelled R1) and an additional pool of CD4+ T cells and B cells as well as CD8+ T cells were CD11b dim (gating labelled R2), indicating that they had significant but lower levels of CD11b expression. Thus, subpopulations of MAIDS-infected CD4+ and CD8+T cells were CD11b bright and dim, respectively, whereas the majority of B cells were positive. Taken together with the fact that CD11b+ cells, and not CD11b− cells, expresses COX-2, this indicates that both B cells and T cells in lymph nodes from MAIDS-infected mice express COX-2.

From looking at intact lymph nodes from MAIDS-infected mice by immunohistochemistry, it is clear that the gross architecture is altered with loss of germinal centers in MAIDS (week 19 post infection) compared to control mice (FIG. 10, c versus a). At higher magnification of slides immunostained for COX-2, it is evident that whereas lymph nodes from control animals only show brown HRP-staining in the ingested material in macrophages (falsely positive "tingible" bodies, FIG. 10b), a large proportion of lymph node cells in MAIDS stain positive for COX-2 (FIG. 10d).

TABLE 6

| Mouse | Medium | Indomethacin | Anti-CD3 | Indomethacin/Anti-CD3 |
|---|---|---|---|---|
| 1 | 1304 | 1412 | 6245 | 9381 |
| 2 | 1082 | 1129 | 8019 | 47926 |
| 3 | 209 | 265 | 918 | 1345 |
| 4 | 236 | 335 | 8938 | 11579 |
| 5 | 4715 | 4317 | 6591 | 8545 |
| 6 | 1799 | ND | 2932 | ND |
| 7 | 3051 | ND | 7436 | ND |
| 8 | 1668 | ND | 3594 | 19624 |
| 9 | 839 | 2363 | 7885 | 31830 |
| 10 | 3413 | 7316 | 8777 | 42244 |
| Median | 1486 | 1412 | 7013 | 15601** |
| (25-75th percentiles) | (839-3051) n = 10 | (335-4317) n = 7 | (3594-8019) n = 10 | (8963-37037) n = 8 |

Indomethacin (Indo) vs. controls; **denotes p < 0.01

Example 3

HIV Patients Exhibit Marginal Effects when Treated with Non-selective COX Inhibitor In vivo Methods Negative Selection of Peripheral Blood CD3+ T Cells from HIV Patients Peripheral blood CD3+ T cells were purified by negative selection from buffycoats from normal healthy donors (Ullevaal University Hospital Blood Center, Oslo, Norway). Briefly, peripheral blood mononuclear cells were isolated by density gradient (Lymphoprep, NycoMed, Oslo, Norway) centrifugation followed by negative selection using monodisperse magnetic beads directly coated with antibodies to CD14 and CD19 and rat anti-mouse IgG beads coated with antibodies to CD56 and a magnet. Magnetic beads were all from Dynal (Oslo, Norway, cat. no. 111.12, 111.04, and 110.11, respectively) whereas anti-CD56 antibody was from Pharmingen (San Diego, Calif., cat. no. 31660.d ). All steps were performed at 4° C. Cell suspensions were analyzed by flow cytometry and shown to consist of more than 90% CD3+ cells.

Proliferation Assays Using HIV Patient T Cells

Proliferation assays were performed by incubation of $0.75 \times 10^6$ CD3+ T cells/ml in a 100 µl volume in flat-bottom 96-well microtiter plates. Activation was achieved by subsequent addition of monodisperse magnetic beads coated with sheep anti-mouse IgG (Dynal, cat. no. 110.02) at a cell:bead ratio of 1:1 followed by addition of anti-CD3 (clone $SpvT_3b$) at a final dilution of 1:125 000 for the experiments shown. The optimal concentration of antibody was titrated carefully in the initial setup and parallel experiments at several different dilutions of antibody were always performed. Proliferation was analyzed by incubating cells for 72 hours during which [$^3$H]-thymidine was included for the last 16 hours. Cells were washed and harvested onto glass filters and subsequently analyzed by β-scintillation counting. CAMP analogs, when used, were added 30 min prior to activation by addition of anti-CD3 antibodies. 8-CPT-cAMP was from Sigma (St. Louis, Mo.).

Experimental

An on-going phase II clinical trial is testing the immunostimulatory effect of short-term treatment with a non-selective COX inhibitor (indomethacin) on surrogate parameters on T cells from HIV infected patients. According to approved protocol, patients were to receive 50 mg indomethacin 3 times a day (total dose of 150 mg/day) for 2 weeks with sampling at day 0, day 14 and day 28 (2 weeks after discontinuation). However, due to adverse events such as epigastrial pain and dyspepsia, and discontinuation of the study among the initial patients, this dose had to be cut back to 25 mg indomethacin 3 times a day (total dose of 75 mg/day). FIG. 11 shows T cell immune function (measured as proliferation after activation) of the 3 patients (pat. 1 to pat 3) that have so far completed the study. The upper panel shows levels of proliferation after T cell activation at start (0 days), at completion of indomethacin treatment (14 days) and 2 weeks thereafter (28 days). As can be seen, patients 1 and 2 did not increase their immune function by a non-selective COX antagonist administered in vivo. However in patient 3, T cell responses increase approximately 2.5-fold and persisted up to 2 weeks after discontinuation of indomethacin. FIG. 11*b*, bottom panel shows T cell proliferation after incubation with a PKA-I selective cAMP antagonist, Rp-8-Br-cAMPS in vitro in cell cultures. The degree of cAMP-mediated T cell dysfunction is evident from the reversal of proliferation obtained by the antagonist (compare upper and lower panels; approx. 2-fold increase in proliferation inpatients 1 and 3 at all time points whereas no effect in patient 2). It is clear from FIG. 11 that indomethacin did not have a convincing effect, which may be attributed to the lack of COX-2 selectivity as well as to dose-limitations due to adverse events.

Example 4

HIV Patients Show Marginal Effects After Administration of Non-Selective Cox Inhibitor In vivo (Continuation of the Experiments of Example 3)

Methods

The methods used were as described in Example 3.

Experimental

Results from 7 patients in an on-going phase II clinical trial (continuation of Example 3) that received indomethacin 25 mg three times a day perorally for 14 days in addition to triple combination therapy is shown in FIG. 12. Patients 1-3 correspond to those described in Example 3. The problem with administration of indomethacin is adverse events as described above (Example 3) that limit the dose to 25 mg three times a day. At this permissive dose, the effects of this non-selective COX inhibitor are marginal. After 14 days of treatment only two of seven patients had clearly elevated T cell immune function measured as proliferation after T cell activation whereas one patient had decreased immune function and four patients had minor changes. Two weeks after discontinuation of indomethacin, five of seven patients had elevated immune responsiveness compared to day 0. However, only two patients had a more than two-fold increase in T cell proliferation.

Example 5

Cox-2 Inhibitors Improve Immune Function of MAIDS T Cells In vitro

Methods

The methods used in the proliferation assay were as described in Example 1. The $PGE_2$ assay was as described in Example 1.

Experimentals

Proliferation Assay

Mixed lymph node cells were isolated from MAIDS mice 17 weeks post-infection. Cells were activated by anti-CD3 antibodies to induce proliferation of T cells, and [$^3$H]-thymidine incorporation was examined after 72 hours as a measure of immune function. Proliferation of cells from MAIDS-infected mice was again only 5 to 20% of the T cell proliferation of uninfected cells (2000 to 12000 cpm in MAIDS cells vs. mean of 55000 cpm in cells from uninfected mice). However, when rofecoxib (FIG. 13) or celecoxib (FIG. 14) were added to the cultures this increased the proliferation of cells from MAIDS-infected mice two- to three-fold in a concentration-dependent manner. In contrast, treatment of control cultures from uninfected mice with rofecoxib or celecoxib did not increase proliferation (0.8- to 1.0-fold increase in the presence of COX-2 inhibitors, i.e. no increase, not shown). In T cells from MAIDS mice, the concentration of rofecoxib and celecoxib that produced a half-maximal effect (ED50) was approximately 0.01 µM for rofecoxib and 0.03 µM for celecoxib. The fact that sub-micromolar concentrations are effective, clearly indicate that the observed increase in immune response is mediated via inhibition of COX-2, and not COX-1 which is inhibited only at micromolar concentrations of rofecoxib and celecoxib (values from Warner et al., 1999, PNAS USA, 96, p7563-7568). Thus, reversal of inhibited T cell immune function by rofecoxib and celecoxib results in decreased $PGE_2$ production in the mixed cultures and thereby lowered T cell cAMP levels via inhibition of COX-2.

$PGE_2$ Production

The effect of the COX-2 inhibitors rofecoxib and celecoxib on $PGE_2$ levels was also analysed. As can be seen from FIG. 15, crude lymph node cells from MAIDS mice secreted 5 to 6-fold more $PGE_2$ than lymph node cells from healthy mice (see also FIG. 6). Furthermore, $PGE_2$ levels in response to LPS increased 8-10 fold in infected compared to approximately 2-fold in uninfected mice. When cells were incubated in the presence of COX-2 inhibitors rofecoxib or celecoxib, the $PGE_2$ secretion of MAIDS lymph node cells was similar to that of uninfected cells. The effect of indomethacin (compar proliferation in FIG. 7) is included as control.

Example 6

Cox-2 Inhibitor Improves Immune Function of MAIDS T Cells In vivo

Methods and Experimental

Infected mice (17 weeks post-infection) were treated for one week per os (i.e. orally) with a dose of rofecoxib corresponding to the recommended dose for use in humans (and taking into account the 7-fold higher clearance in rodents).

MAIDS mice normally develop an immunoproliferation syndrome with enlarged lymph nodes and spleen. In accordance with this, untreated infected animals had an average spleen weight of 1.3 g and an average weight of pooled lymph nodes of 1.7 g. In contrast MAIDS mice receiving rofecoxib for 7 days had average spleen weights of 0.8 g and average weight of pooled lymph nodes of 0.3 g, indicating reversal of lymphoproliferation.

The results are shown in FIG. 16. When T cell immune function was assessed in crude lymph node cells from infected treated and untreated mice, it was clear that whereas untreated infected animals had anti-CD3 induced proliferation in the range of 2000 to 10000 cpm (average 7300 cpm), infected mice that received rofecoxib for one week had T cell responses to anti-CD3 that were increased 2.7- to 5.6-fold compared to infected, untreated mice. Furthermore, whereas infected, untreated mice demonstrated increased anti-CD3 induced T cell proliferation in the presence of Rp-8-Br-cAMPS, this 2- to 3-fold effect was lost in the mice treated with rofecoxib, indicating that the treatment with rofecoxib in vivo lowered $PGE_2$ levels and reversed cAMP-mediated inhibition of T cell function.

Example 7

In vivo Treatment of MAIDS Mice with Rofecoxib or Celecoxib Increases T-Cell Responses to Anti-CD3 and Immune Responses Methods and Experimental Infected mice were treated with rofecoxib and celecoxib corresponding to the recommended dose for use in humans (and taking into account the 7-fold higher clearance in rodents, 3 and 20 mg/kg/day, respectively). Parenteral administration was accomplished by intraperitoneally injecting Cox-2 inhibitors formulated in intralipid. The results are shown in FIG. 17.

When T cell immune function was assessed in crude lymph node cells from infected treated and untreated mice after 18 to 20 days of infection, it was clear that whereas untreated infected animals had anti-CD3 induced proliferation in the range of 10000 cpm, infected mice that received rofecoxib for 18 to 20 days had T cell responses to anti-CD3 that were increased approximately two-fold compared to infected, untreated mice. Similarly, celecoxib improved immune responses in cells from the majority of the group of mice injected to approximately 3-fold over untreated, uninfected mice.

Example 8

In vivo Treatment of MAIDS Mice with Meloxicam Increases T-cell Immune Function

Methods and Experimental

Infected and healthy mice were treated with 2.8 mg/kg/day meloxicam, which corresponds to the recommended dose for use in humans when taking into account the 7-fold higher clearance in rodents. Parenteral administration was accomplished by subcutaneous implantation of osmotic pumps filled with water-soluble meloxicam injection compound. T cell function was assessed and the results are shown in FIG. 18.

When T cell immune function was assessed in crude lymph node cells from treated and control (PBS)-treated infected mice after 2 weeks of treatment, it was clear that whereas PBS-treated, infected animals had anti-CD3 induced proliferation in the range of 500 cpm, infected mice that received meloxicam for 14 days had T cell immune responses to anti-CD3 that were significantly increased compared to infected mice that received only PBS (FIG. 18*a*, more than 10-fold; p<0.05).

When meloxicam was added back to the cell cultures during the 3-day in vitro T cell proliferation assay to prevent release from the in vivo inhibition by meloxicam and thereby reactivation of COX-2, the immune response in the meloxicam-treated group was two-fold higher than without addition of meloxicam in vitro (p=0.005) and compared to that of MAIDS mice that received PBS in vivo the effect was again significant (FIG. 18*b*, p<0.05).

In contrast, only MAIDS mice that received PBS in vivo and not meloxicam-treated mice demonstrated increased immune responses when the PKA type I-selective cAMP antagonist, Rp-8-Br-cAMPS, was added to the anti-CD3 stimulated mixed lymph node cultures in vitro (FIG. 18*c*). The fact that the effect of cAMP antagonist is absent in meloxicam-treated MAIDS mice indicates that in vivo meloxicam treatment reduces or removes the cAMP-induced immunodeficiency of MAIDS and restores immune function.

The invention claimed is:

1. A method of reducing or alleviating T-cell dysfunction in a human with HIV infection or AIDS comprising administering a COX-2 inhibitor, or derivative or pharmaceutically acceptable salt thereof, which inhibits the enzymatic activity of COX-2, to a patient in need thereof, wherein the COX-2 inhibitor is a compound of general formula B:

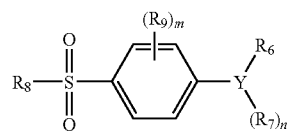

B wherein
Y represents oxazolyl, isoxazolyl, thienyl, dihydrofuryl, furyl, pyrrolyl, pyrazolyl, thiazolyl, imidazolyl, isothiazolyl, cyclopentenyl, phenyl or pyridyl;
n is an integer from 0 to 3;
m is an integer from 0 to 4;
$R_6$ represents a ketocycly, cycloalkyl or aryl group, which group may optionally be substituted by one or more halogen atoms, or by a methyl group;
$R_7$ each independently represent hydrogen, halogen atom, oxo group, acyl group, or alkyl group optionally substituted by one or more or more fluorine atoms;
$R_8$ represents an alkyl group or —$NHR_{10}$;
$R_9$ represents a halogen atom; and
$R_{10}$ represents a hydrogen atom or an optionally substituted alkyl group;
or a derivative or a pharmaceutically acceptable salt thereof.

2. The method of claim 1, wherein the COX-2 inhibitor has a WHMA $IC_{80}$ COX-1/COX-2 selectivity ratio greater than 5.

3. The method of claim 1 wherein $R_8$ is —$NH_2$ or —$CH_3$.

4. The method of claim 1, wherein Y is a pyrazolyl, furyl or thienyl group.

5. The method of claim 1, wherein $R_6$ is an aryl group optionally substituted with one or more fluorine atoms.

6. The method of claim 1, wherein n is 1 or 2.

7. The method of claim 1, wherein $R_7$ is a bromine atom.

8. The method of claim 1, wherein the COX-2 inhibitor is selected from the group consisting of celecoxib, rofecoxib, DuP-697, SC-58125, DFU, MF tricyclic, JTE-522, 4-(2-oxo-3-phenyl-2,3-dihydrooxazol-4-yl)-benzenesulfonamide, etoricoxib, valdecoxib, and paracoxib sodium.

9. The method of claim 1, wherein the COX-2 inhibitor is rofecoxib.

10. The method of claim 1, wherein the COX-2 inhibitor is celecoxib.

11. The method of claim 1, wherein the COX-2 inhibitor is administered in conjunction with one or more additional active ingredients, wherein the COX-2 inhibitor and additional active ingredients are administered simultaneously, separately or sequentially.

12. The method of claim 1, wherein the COX-2 inhibitor is administered in conjunction with one or more additional active ingredients, the COX-2 inhibitor and additional active ingredients are administered simultaneously, separately or sequentially, and at least one of the additional active ingredients is a COX-2 inhibitor.

13. The method of claim 1, wherein the COX-2 inhibitor has a WHMA $IC_{80}$ COX-1/COX-2 selectivity ratio greater than 50.

14. The method of claim 1, wherein $R_6$ is a ketocyclyl, cycloalkyl or aryl group substituted by one or more halogen atoms.

15. The method of claim 1, wherein $R_{10}$ is an acyl group.

16. The method of claim 1, wherein the T-cell dysfunction is characterized by a reduced ability of T cells from the human with HIV infection or AIDS, relative to the T cells of an uninfected human, to proliferate in vitro in response to TCR/CD3-stimulation.

17. The method of claim 16, wherein the T cells from the human with HIV infection or AIDS proliferate in response to TCR/CD3-stimulation at a level less than 20% of that of the uninfected human.

18. The method of claim 1, wherein the COX-2 inhibitor is administered orally.

19. The method of claim 1, wherein the method further comprises, as an initial step, a step of determining that the human has T cell dysfunction.

20. The method of claim 19, wherein it is determined that the T cells from the human with HIV infection or AIDS proliferate in vitro in response to TCR/CD3-stimulation at a level less than 20% of that of the uninfected human.

21. The method of claim 1, wherein the method further comprises, as an initial step, a step of determining that the human is infected with HIV.

22. The method of claim 1, wherein the COX-2 inhibitor is selected from the group comprising SC-58125, DFU, MF tricyclic, JTE-522, valdecoxib, paracoxib sodium, and etoricoxib.

23. The method of claim 22, wherein the COX-2 inhibitor is selected from the group comprising valdecoxib, paracoxib sodium, and etoricoxib.

* * * * *